(12) United States Patent
Singh et al.

(10) Patent No.: US 9,289,194 B2
(45) Date of Patent: Mar. 22, 2016

(54) INSERT AND INSERT SYSTEM FOR A LAPAROSCOPIC INSTRUMENT

(71) Applicants: Jai Singh, Woodvale (AU); Jiwan Steven Singh, Woodvale (AU)

(72) Inventors: Jai Singh, Woodvale (AU); Jiwan Steven Singh, Woodvale (AU)

( * ) Notice: Subject to any disclaimer, the term of this patent is extended or adjusted under 35 U.S.C. 154(b) by 235 days.

(21) Appl. No.: 13/720,055

(22) Filed: Dec. 19, 2012

(65) Prior Publication Data

US 2013/0178865 A1 Jul. 11, 2013

Related U.S. Application Data

(60) Provisional application No. 61/583,755, filed on Jan. 6, 2012, provisional application No. 61/701,883, filed on Sep. 17, 2012.

(51) Int. Cl.
*A61B 17/04* (2006.01)
*A61B 17/00* (2006.01)
(Continued)

(52) U.S. Cl.
CPC .......... *A61B 17/00234* (2013.01); *A61B 17/00* (2013.01); *A61B 17/0218* (2013.01); *A61B 17/0469* (2013.01); *A61B 17/0483* (2013.01); *A61B 17/3211* (2013.01); *A61B 17/3213* (2013.01); *A61B 17/320016* (2013.01); *A61B 17/42* (2013.01); *A61B 17/4241* (2013.01);
(Continued)

(58) Field of Classification Search
CPC .............. A61B 5/150267; A61B 2017/00464; A61B 2017/00473; A61B 2017/2927; A61B 2017/2931; A61B 2017/2939; A61B 2017/294; A61B 2017/22072; A61B 2017/320044; A61B 2017/320056; A61B 17/3211; A61B 17/3213; A61B 17/00; A61B 17/00234; A61B 17/0218; A61B 17/0469; A61B 17/0483; A61B 17/320016; A61B 17/42; A61B 2017/00349; A61B 2017/00805; A61B 2017/0237; A61B 2017/06042; A61B 2017/2933; A61B 2017/2934; A61B 2017/2936; A61B 2017/2947; A61B 2019/5437
USPC ............. 606/1, 148, 167, 170, 174, 190, 205, 606/208
See application file for complete search history.

(56) References Cited

U.S. PATENT DOCUMENTS 3,877,434 A * 4/1975 Ferguson et al. ............. 606/158
4,579,116 A * 4/1986 Catalano ....................... 606/107
(Continued)

FOREIGN PATENT DOCUMENTS

WO WO 2013/102235 7/2013

OTHER PUBLICATIONS

PCT Search Report and Written Opinion from the International Searching Authority, dated Feb. 4, 2013, in 9 pages, regarding International Application No. PCT/AU2012/001515.

*Primary Examiner* — Ryan J Severson
*Assistant Examiner* — Christian Knauss
(74) *Attorney, Agent, or Firm* — Knobbe Martens Olson & Bear LLP

(57) ABSTRACT

An insert 30 comprises a rod 32 having a proximal end 34 and a distal end 36. The insert 30 also comprises a tool 38 which is demountably coupled to the distal end 36. Proximal end 34 is formed with a ball 40 which is configured to seat and engage in a socket of a handle 12 of a laparoscopic instrument 10. The rod 32 fits within a sheath 14 of the laparoscopic instrument 10. The distal end 36 of the rod 32 is provided with an attachment head 42 to facilitate the attachment of the tool 38. A linkage mechanism 44 in the attachment head 42 converts the linear motion of the insert 30 (and in particular rod 32) relative to the outer sheath 14 to a pivotal motion.

21 Claims, 21 Drawing Sheets

(51) Int. Cl.
*A61B 17/42* (2006.01)
*A61B 17/02* (2006.01)
*A61B 17/32* (2006.01)
*A61B 17/3211* (2006.01)
*A61B 17/3213* (2006.01)
A61B 17/06 (2006.01)
A61B 17/29 (2006.01)
A61B 19/00 (2006.01)

(52) U.S. Cl.
CPC .............. *A61B2017/00349* (2013.01); *A61B 2017/00464* (2013.01); *A61B 2017/00473* (2013.01); *A61B 2017/00805* (2013.01); *A61B 2017/0237* (2013.01); *A61B 2017/06042* (2013.01); *A61B 2017/2927* (2013.01); *A61B 2017/320056* (2013.01); *A61B 2019/5437* (2013.01)

(56) References Cited

U.S. PATENT DOCUMENTS

| | | | | |
|---|---|---|---|---|
| 4,763,669 A * | 8/1988 | Jaeger | | 600/564 |
| 4,867,139 A * | 9/1989 | Girzadas | | 600/210 |
| 4,959,067 A * | 9/1990 | Muller | | 606/190 |
| 4,963,147 A * | 10/1990 | Agee et al. | | 606/170 |
| 5,112,346 A | 5/1992 | Hiltebrandt et al. | | 606/170 |
| 5,156,633 A * | 10/1992 | Smith | | 606/205 |
| 5,339,801 A * | 8/1994 | Poloyko et al. | | 600/214 |
| 5,352,219 A * | 10/1994 | Reddy | | 606/1 |
| 5,358,507 A * | 10/1994 | Daily | | 606/159 |
| 5,370,659 A * | 12/1994 | Sakashita | | 606/205 |
| 5,403,328 A * | 4/1995 | Shallman | | 606/144 |
| 5,486,183 A * | 1/1996 | Middleman et al. | | 606/127 |
| 5,501,690 A | 3/1996 | Measamer et al. | | |
| 5,514,157 A * | 5/1996 | Nicholas et al. | | 606/206 |
| 5,569,283 A * | 10/1996 | Green et al. | | 606/170 |
| 5,571,119 A * | 11/1996 | Atala | | 606/146 |
| 5,571,126 A * | 11/1996 | Dorsey, III | | 606/167 |
| 5,586,990 A * | 12/1996 | Hahnen et al. | | 606/170 |
| 5,792,165 A * | 8/1998 | Klieman et al. | | 606/170 |
| 6,086,606 A | 7/2000 | Knodel et al. | | |
| 6,093,155 A * | 7/2000 | Ouchi | | 600/569 |
| 6,096,026 A * | 8/2000 | Schultz | | 606/1 |
| 6,099,538 A * | 8/2000 | Moses et al. | | 606/144 |
| 6,193,737 B1 * | 2/2001 | Ouchi | | 606/174 |
| 6,755,815 B2 * | 6/2004 | Schultz | | 606/1 |
| 7,520,886 B2 * | 4/2009 | Surti | | 606/170 |
| RE44,883 E * | 5/2014 | Cha | | 606/80 |
| 2002/0013570 A1 * | 1/2002 | Ruegg et al. | | 606/1 |
| 2002/0120253 A1 * | 8/2002 | Ouchi | | 606/1 |
| 2003/0100914 A1 * | 5/2003 | O'Heeron et al. | | 606/185 |
| 2003/0176874 A1 * | 9/2003 | Sauer | | 606/144 |
| 2004/0249411 A1 * | 12/2004 | Suzuki | | 606/205 |
| 2005/0113838 A1 * | 5/2005 | Phillips et al. | | 606/80 |
| 2005/0203561 A1 * | 9/2005 | Palmer et al. | | 606/190 |
| 2006/0020274 A1 * | 1/2006 | Ewers et al. | | 606/148 |
| 2006/0264976 A1 * | 11/2006 | Terry et al. | | 606/148 |
| 2007/0213749 A1 * | 9/2007 | Kogasaka et al. | | 606/153 |
| 2008/0082105 A1 * | 4/2008 | Chu | | 606/99 |
| 2008/0154297 A1 * | 6/2008 | Lee et al. | | 606/190 |
| 2008/0221586 A1 * | 9/2008 | Garcia-Bengochea et al. | | 606/108 |
| 2008/0294192 A1 * | 11/2008 | Stefan et al. | | 606/205 |
| 2010/0057087 A1 * | 3/2010 | Cha | | 606/80 |
| 2010/0076502 A1 * | 3/2010 | Guyer et al. | | 606/86 R |
| 2011/0264079 A1 * | 10/2011 | Doll | | A61B 17/4241 606/1 |
| 2011/0270291 A1 * | 11/2011 | Nakamura | | 606/167 |
| 2012/0179146 A1 * | 7/2012 | Fan et al. | | 606/1 |

\* cited by examiner

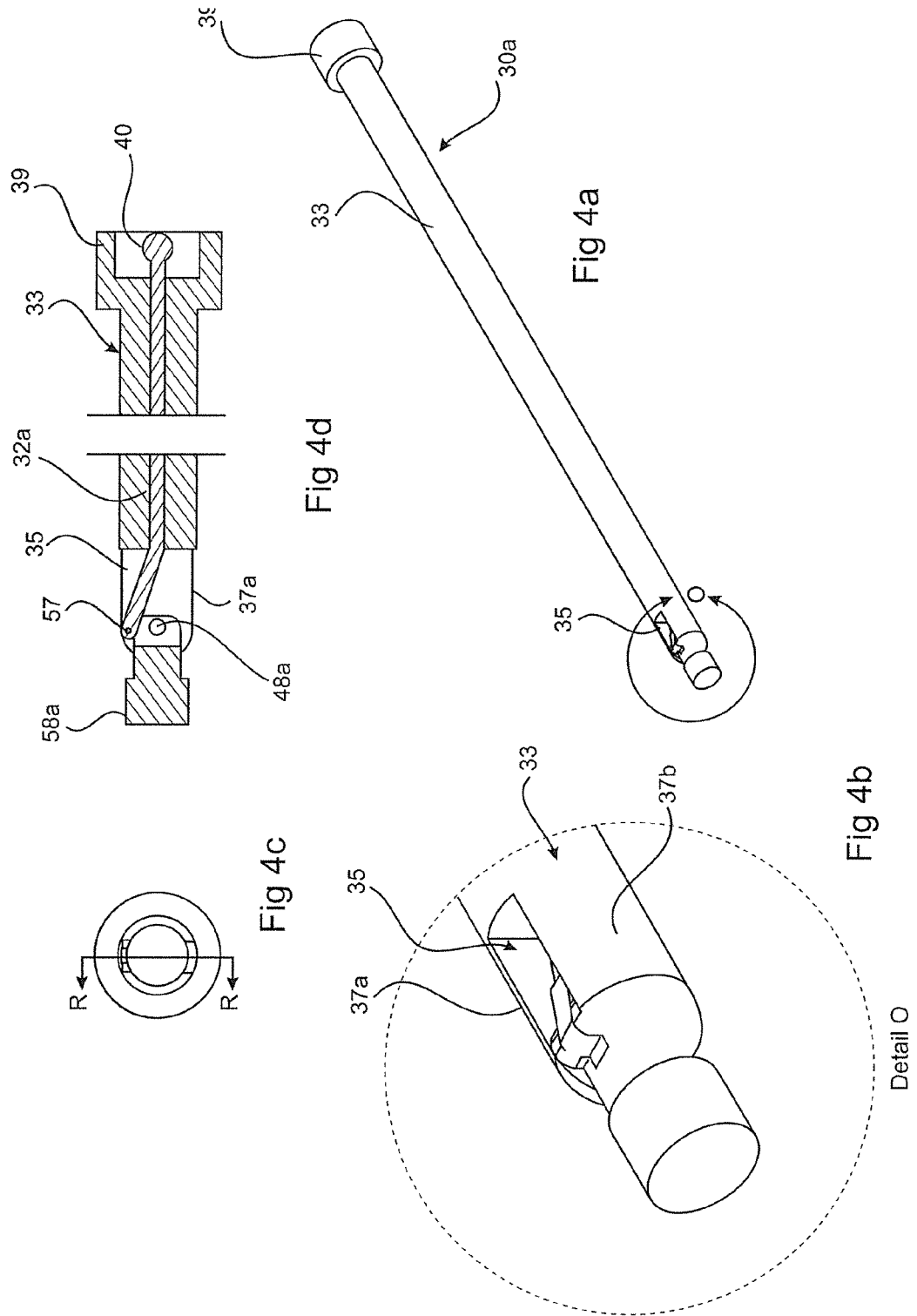

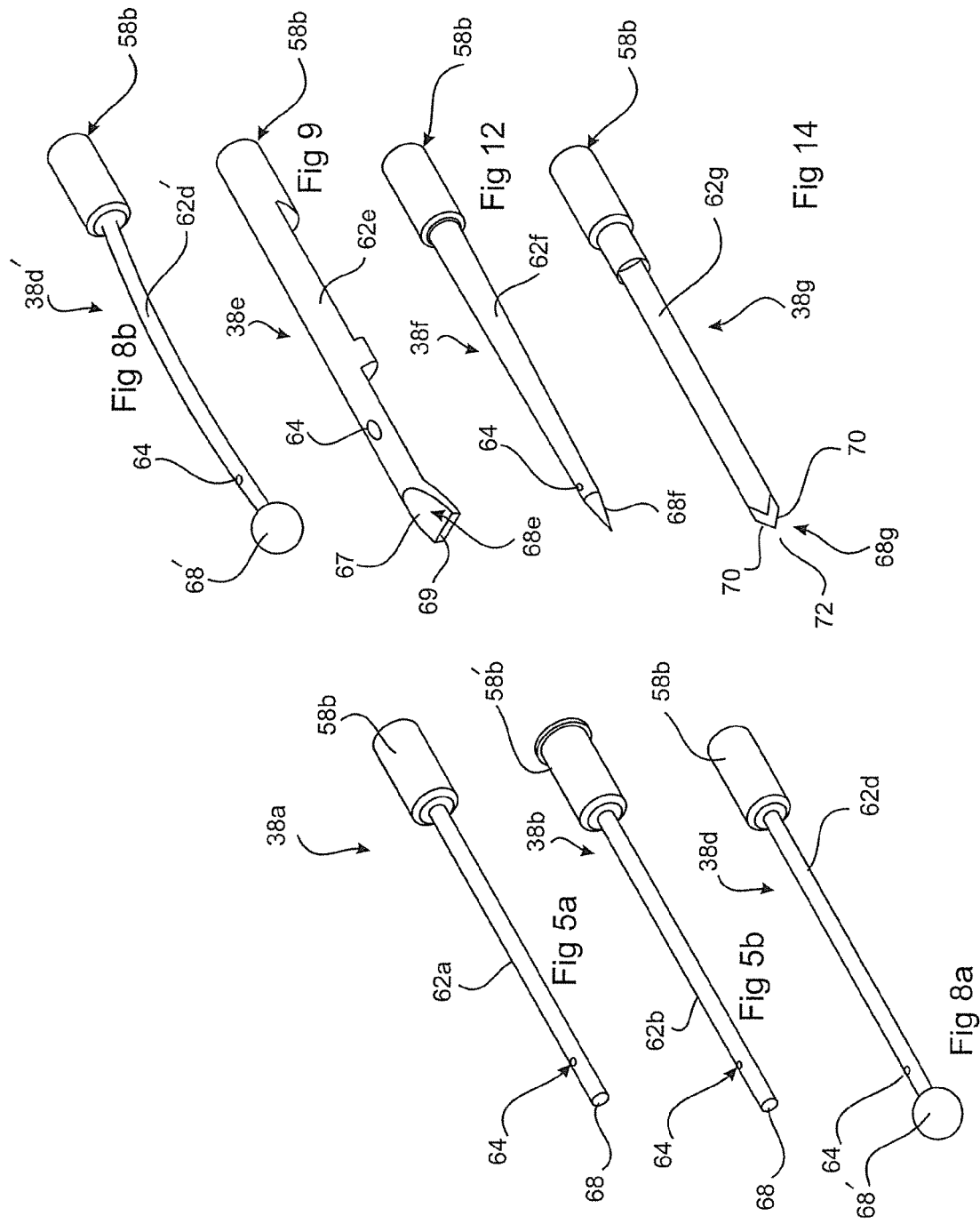

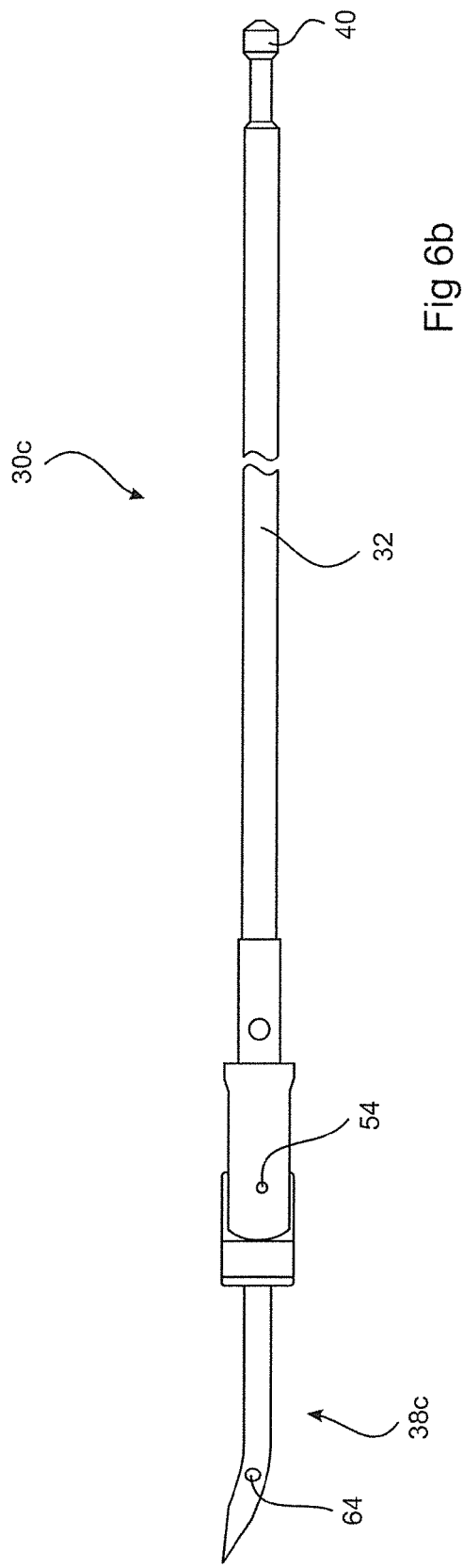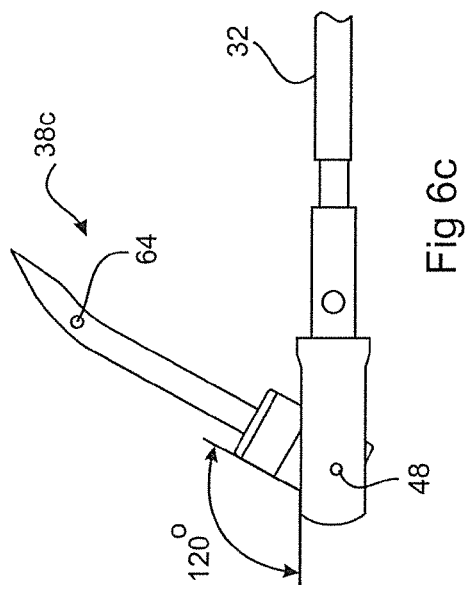

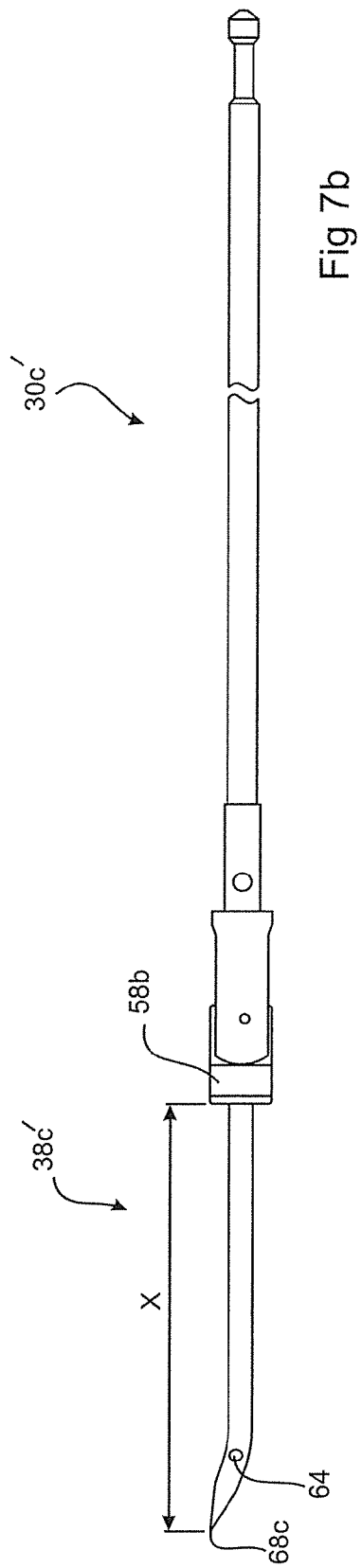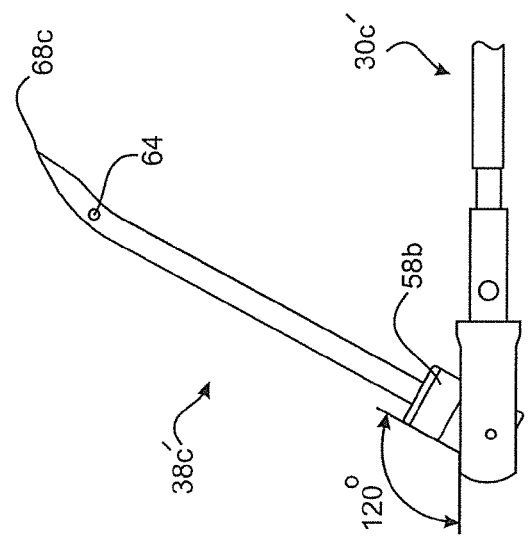

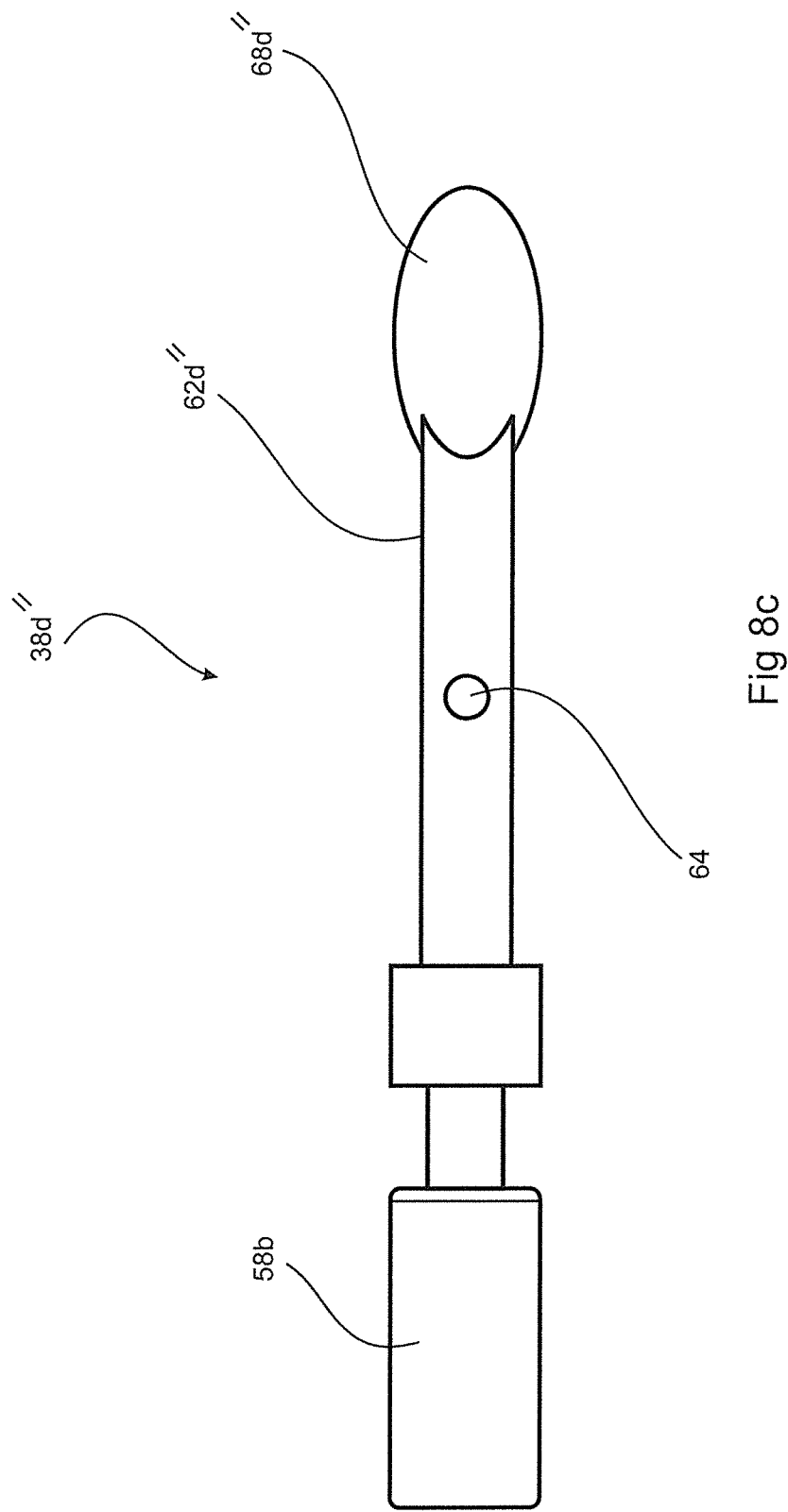

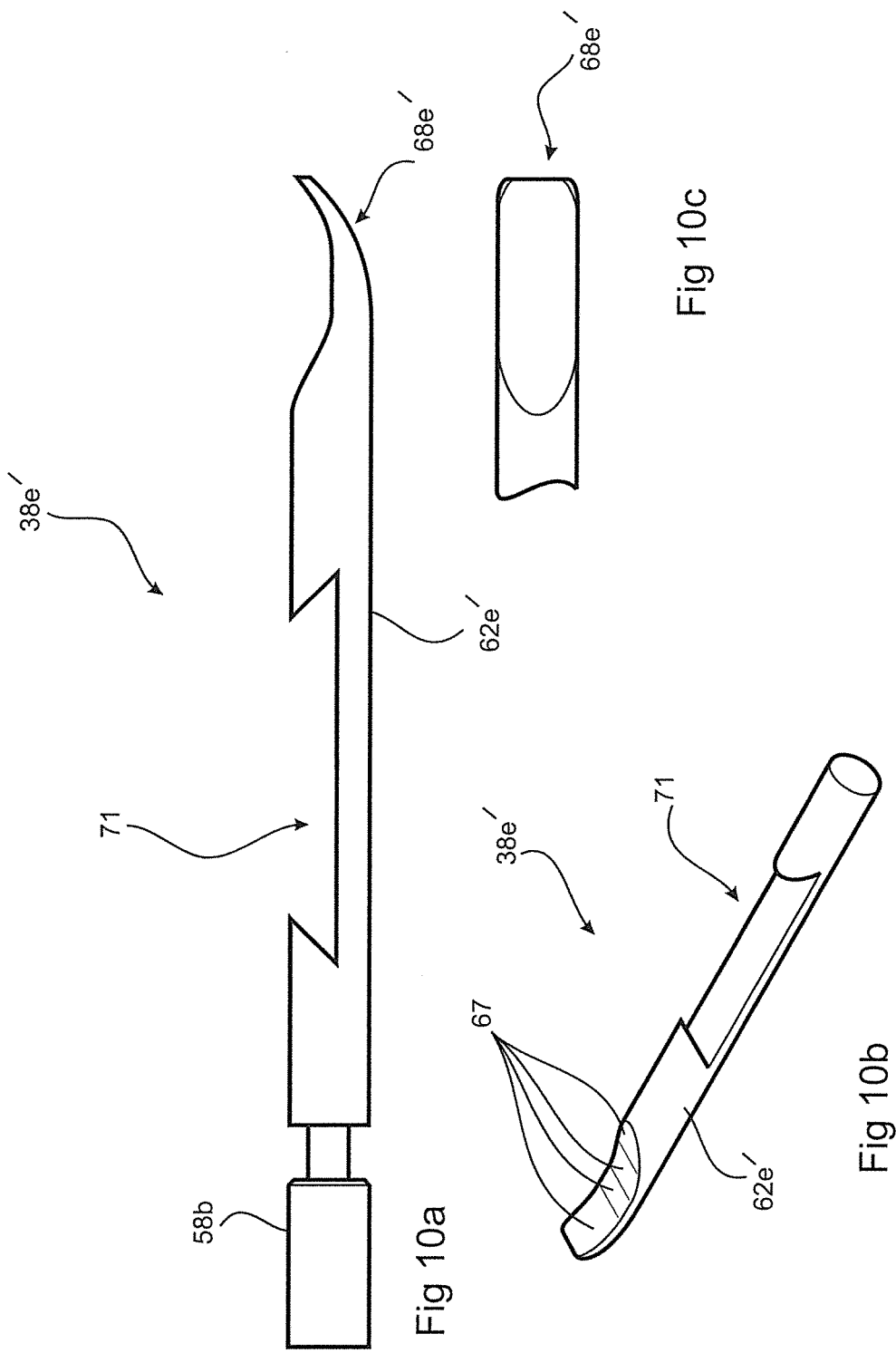

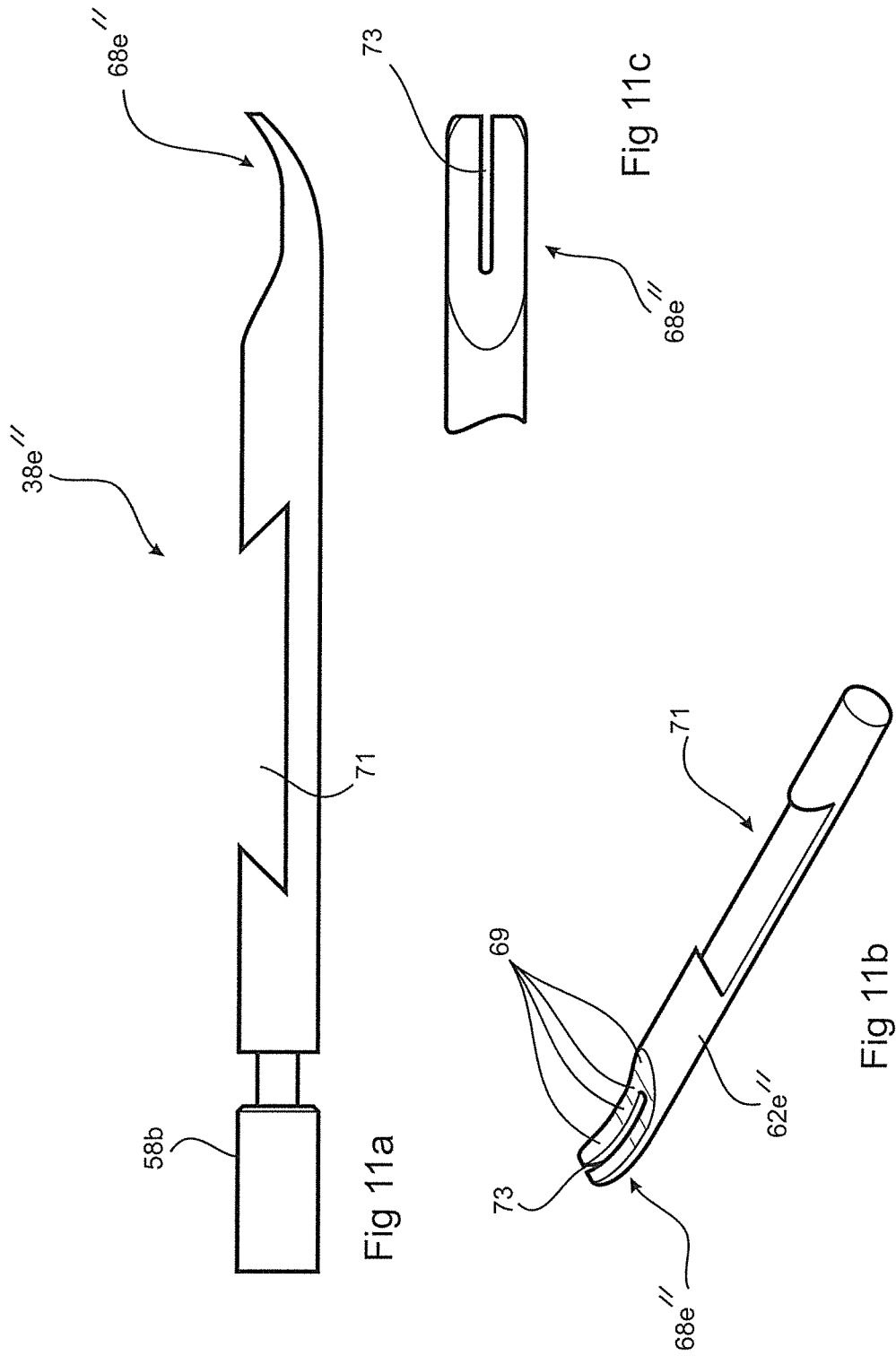

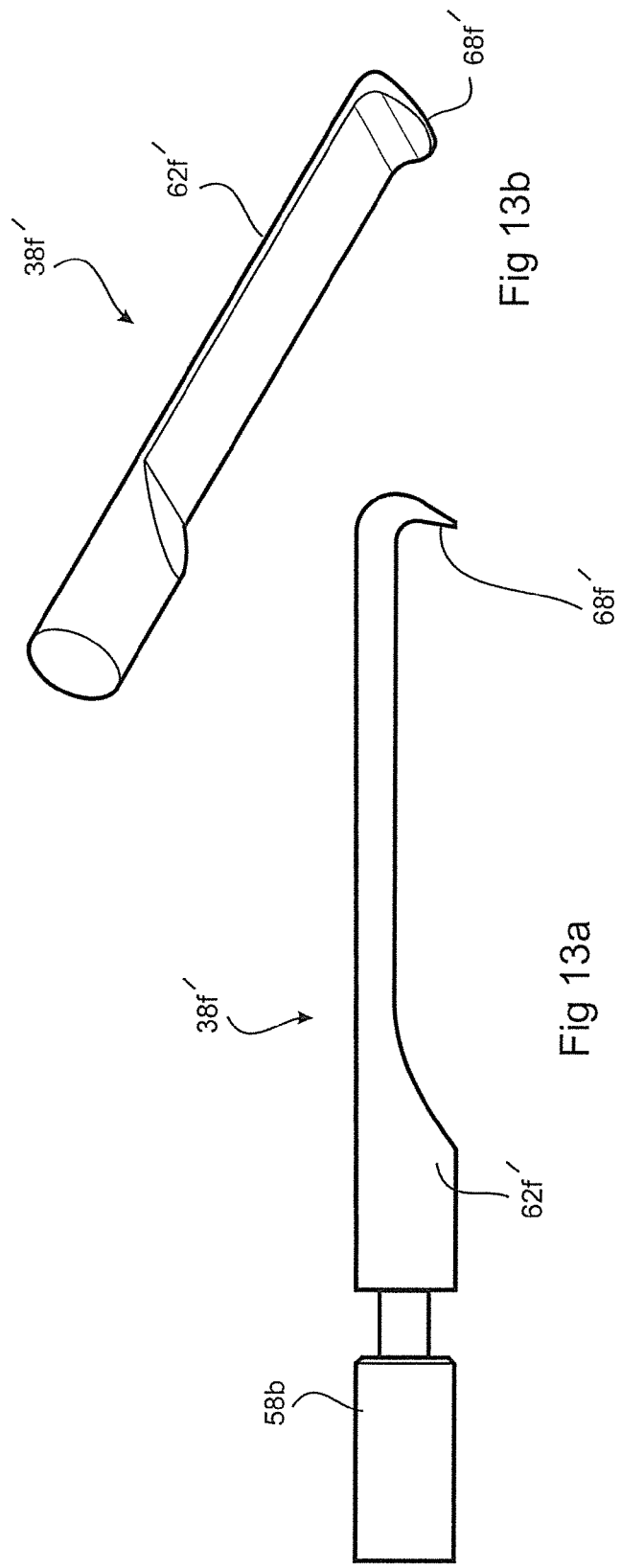

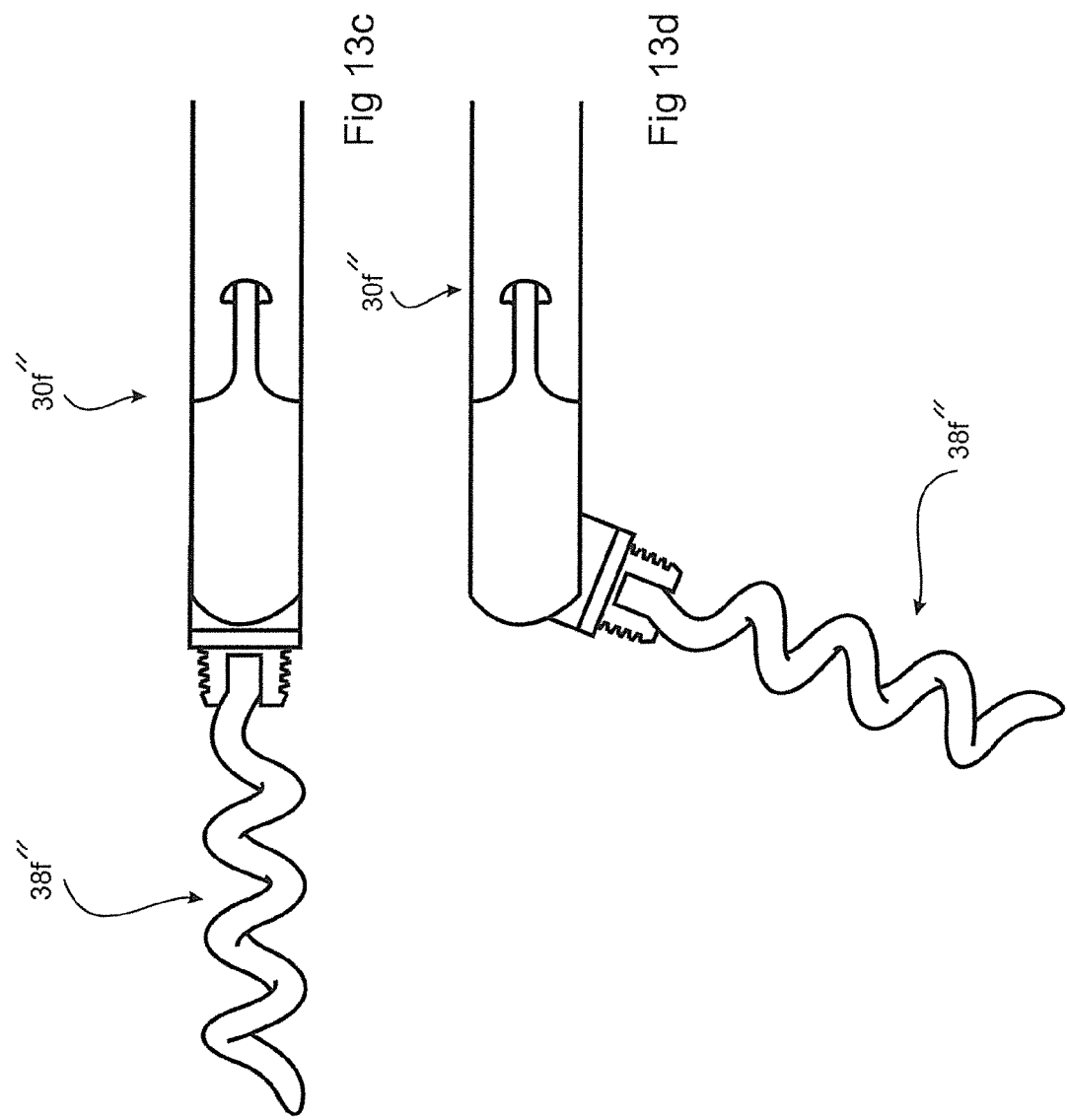

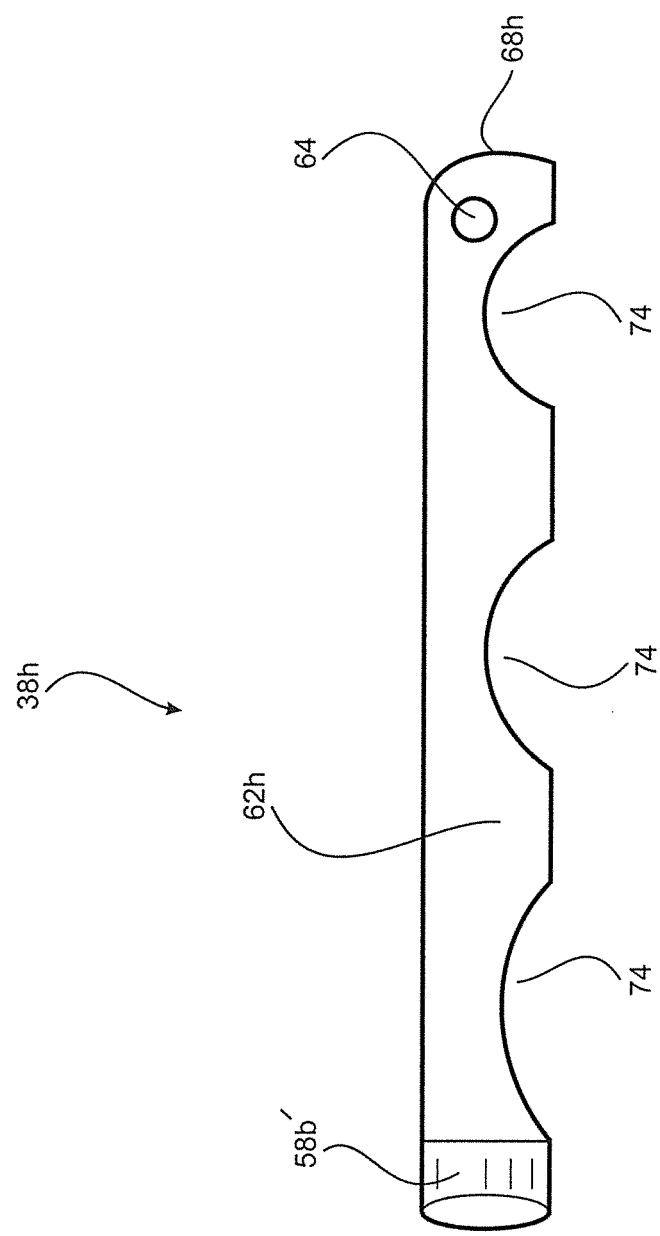

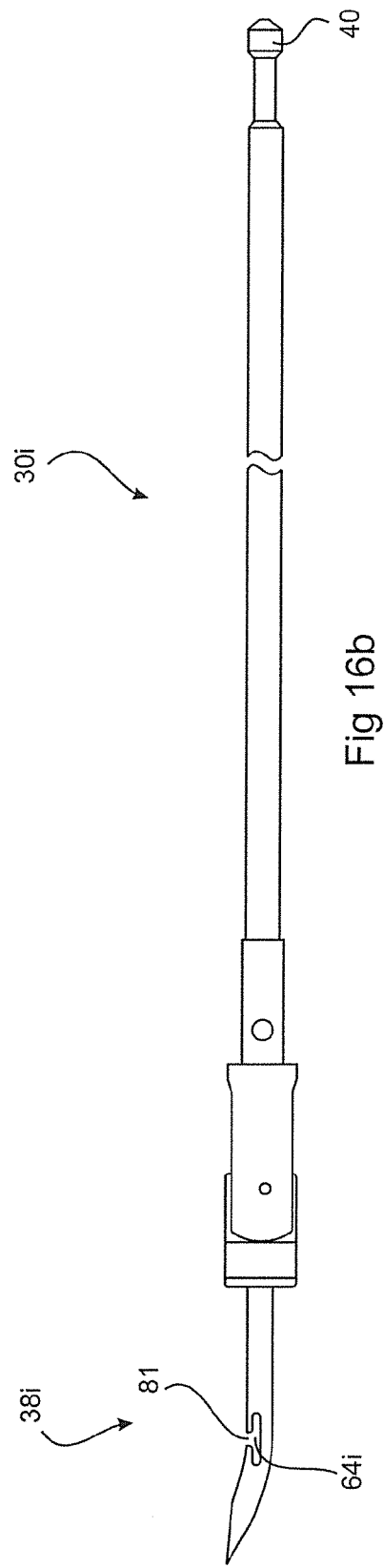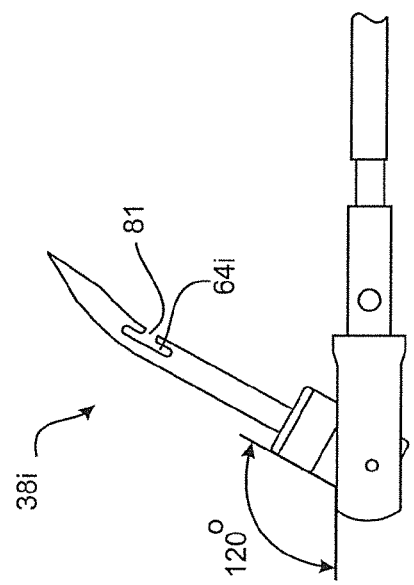

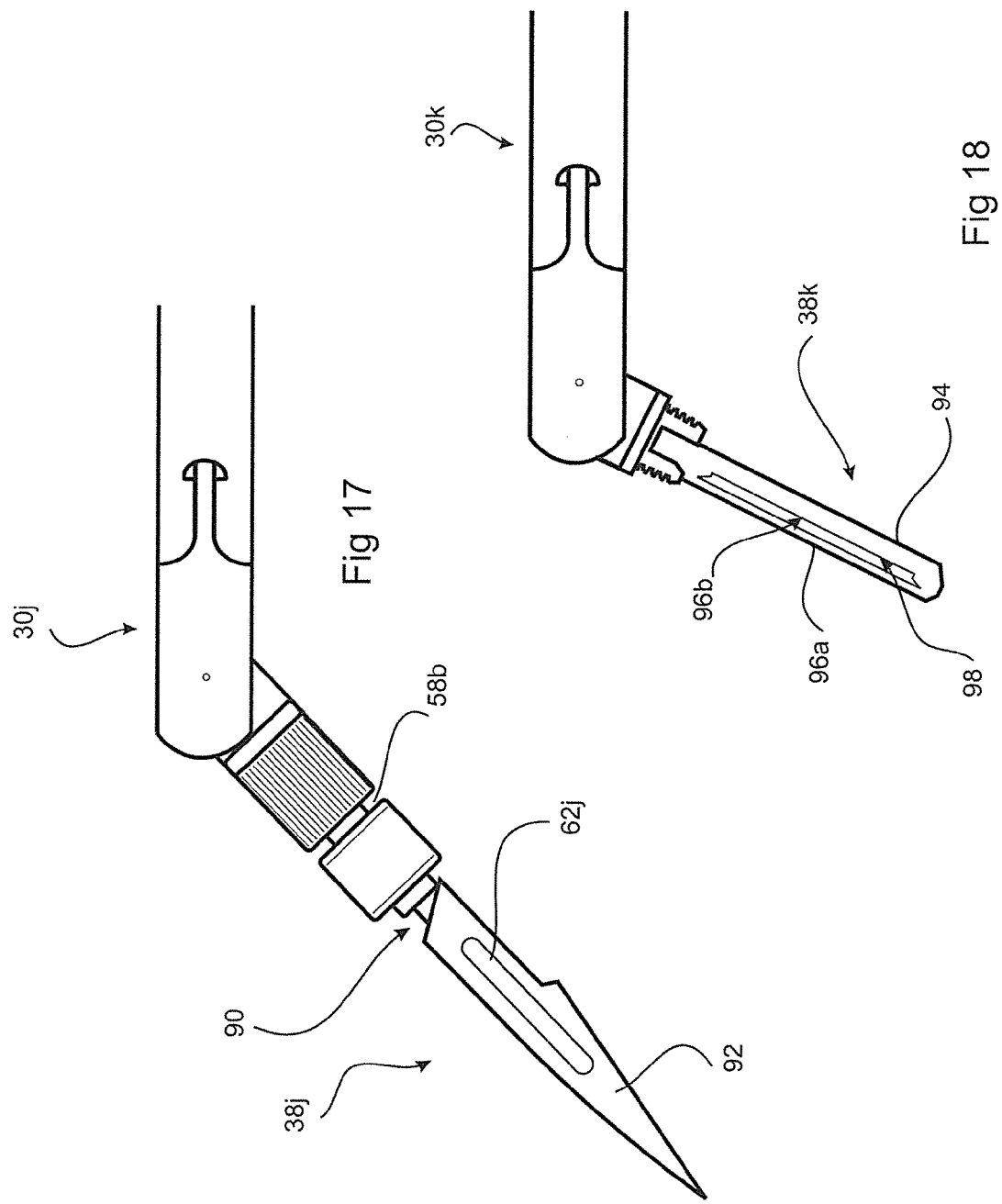

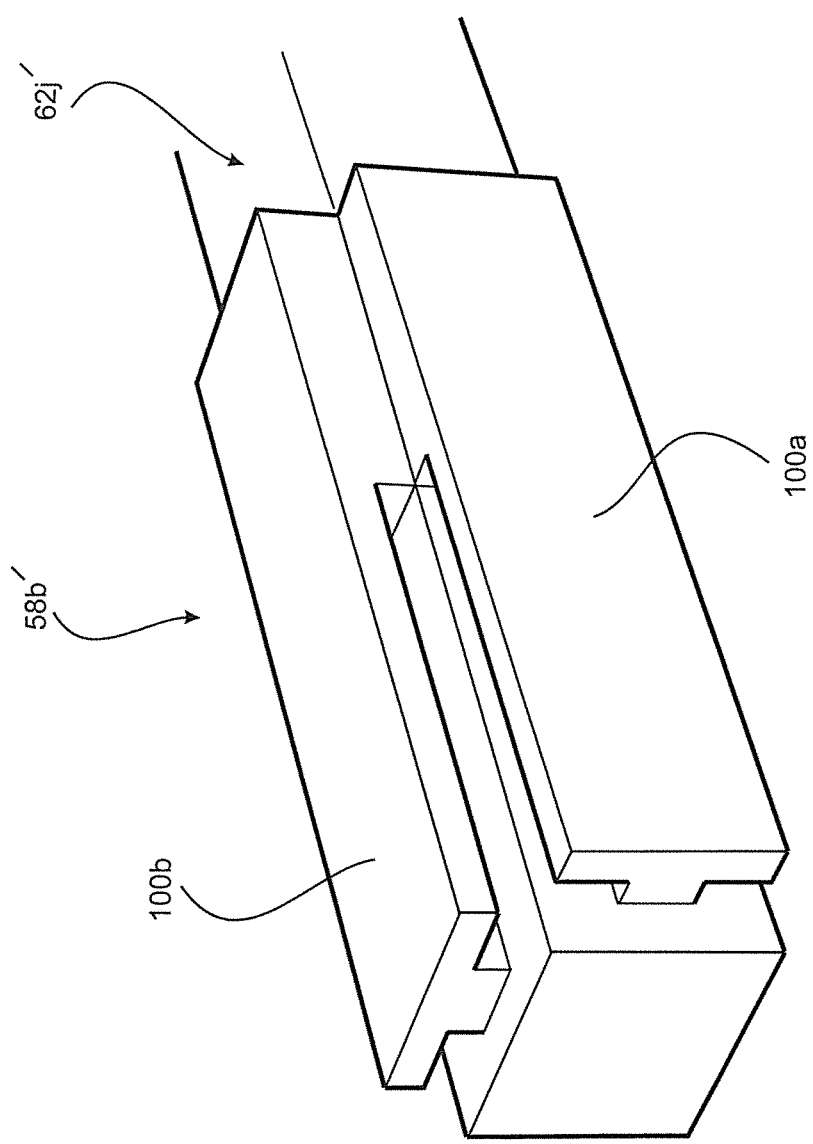

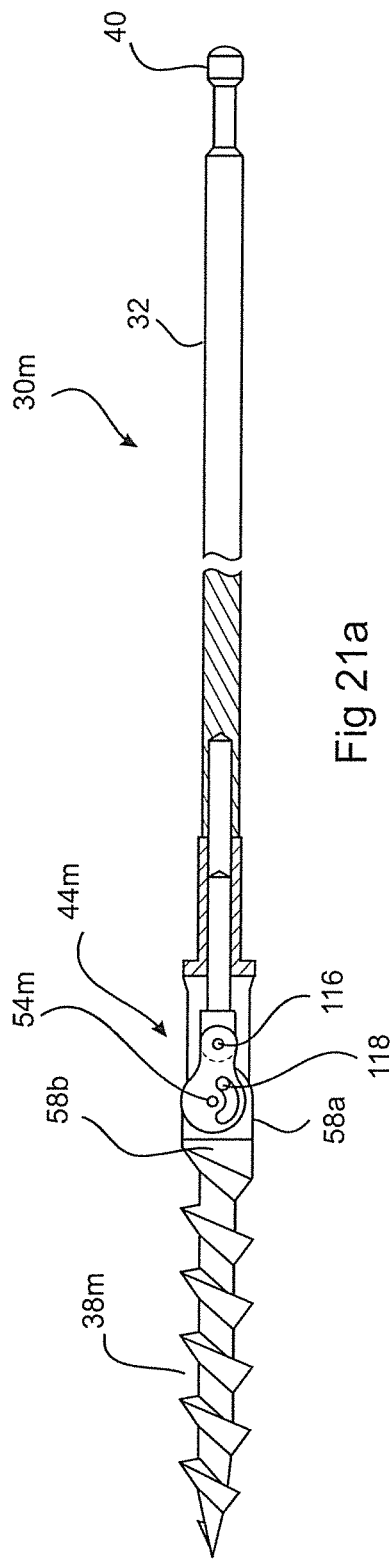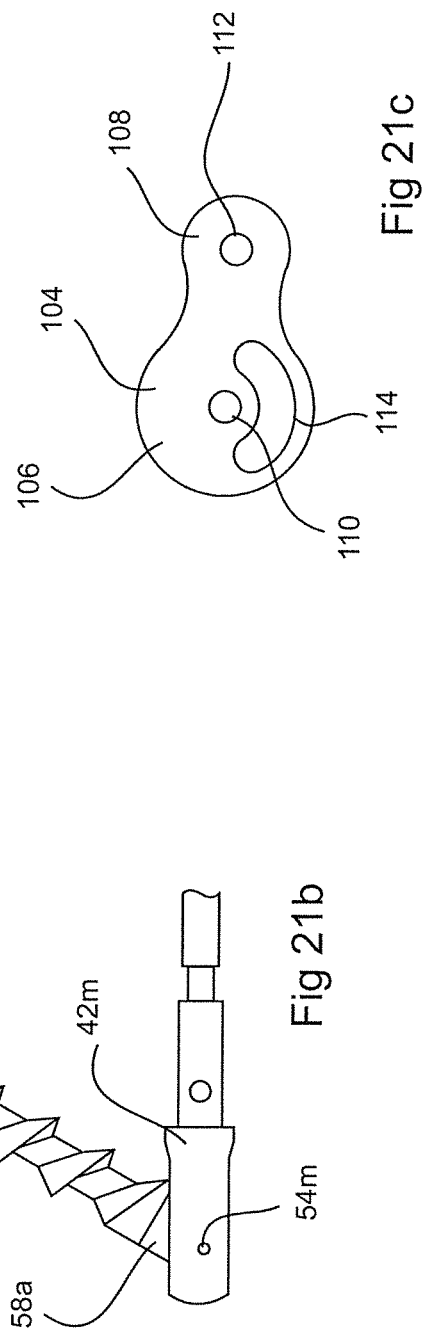

INSERT AND INSERT SYSTEM FOR A LAPAROSCOPIC INSTRUMENT

CROSS-REFERENCE TO RELATED APPLICATION

This application claims the benefit of U.S. Provisional Application Ser. No. 61/583,755 filed on Jan. 6, 2012 and U.S. Provisional Application Ser. No. 61/701,883 filed on Sep. 17, 2012, the contents of which applications are herein incorporated by reference in their entirety.

FIELD OF THE INVENTION

The present invention relates to an insert and an insert system for a laparoscopic instrument.

BACKGROUND OF THE INVENTION

A laparoscopic instrument comprises a handle, an outer sheath, and an insert. The outer sheath may be fixed to or alternately detachable from the handle. The insert extends through the sheath and is operatively coupled to the handle. The handle has two finger rings similar to a regular pair of scissors. When the handle is manipulated by squeezing together the finger rings or pushing them apart the insert is moved linearly relative to the outer sheath. The insert is provided at its distal end with an integrated tool. Linear motion of the insert relative to the sheath operates the tool. This may be manifested for example by the opening and closing of jaws or blades of the tool. The function and nature of this tool determines the type of insert. Types of inserts include scissors, dissectors, forceps and needle holders. Moreover, there are many variations within each type of insert. For example, scissor inserts are available as straight, curved, fine, parrot beak, serrated, single or double action scissor inserts. Dissector inserts are available as duck bill, Maryland, round nose, bottle nose, and mixter.

Depending on the type of laparoscopic surgery at hand, a surgeon will require a large range of laparoscopic instruments with specific inserts.

Also, while there are currently many different types of inserts available, some of these inserts require very high levels of surgical expertise and competence in order to avoid accidental injury to patients. Indeed the level of expertise required while maintaining patient safety may at times be beyond many surgeons.

SUMMARY OF THE INVENTION

In one aspect the invention provides an insert for a laparoscopic instrument having a handle and an outer sheath coupled to the handle, the insert comprising:
a rod configured to fit within the outer sheath and engage at its proximal end the handle; and
a tool demountably coupled to a distal end of the rod.

In one embodiment the insert comprises a linkage mechanism which converts linear motion of the rod relative to the outer sheath to a pivotal motion of, or a component of, the tool of up to at least 150°.

In one embodiment the tool is provided with a suture aperture opening for receiving a suture.

In one embodiment the suture opening is either a suture hole or a suture slot wherein the suture slot extends along a length of the tool and is provided with an opening enabling a suture material to enter the suture slot.

In one embodiment the tool comprises a suture needle.

In one embodiment the needle comprises a straight shaft.

In one embodiment the needle comprises a curved shaft.

In one embodiment a distal end of the needle: (a) tapers conically to a point; (b) tapers linearly to a point to produce a cutting edge; or (c) is provided with a rounded end.

In one embodiment the tool comprises a ureteric tunneller having either a straight shaft provided with one of a spherical tip or an ellipsoid tip; or curved shaft provided with one of a spherical tip or an ellipsoid tip.

In one embodiment the tool comprises a dissector.

In one embodiment the dissector comprises a shaft, a reduced thickness tip at a distal end of the shaft and a straight edge at a distal end of the tip lying perpendicular to a length of the shaft.

In one embodiment the reduced thickness tip has at least one planar surface.

In one embodiment the reduced thickness tip is curved in configuration.

In one embodiment insert comprises a longitudinal slot formed in the reduced thickness tip and opening onto the straight edge.

In one embodiment the shaft is provided with a dovetail shaped slot extending along a longitudinal axis of the shaft and inboard of the tip.

In one embodiment the tool comprises a myoretractor having either a straight shaft or a corkscrew shaped shaft.

In one embodiment the tool comprises a myoretractor having a straight shaft and a hook at a distal end of the shaft.

In one embodiment the tool comprises a scalpel.

In one embodiment the tool comprises a peeling blade provided with a longitudinal slot the slot having mutually facing longitudinal cutting edges.

In a second aspect the invention provides an insert system for a laparoscopic instrument having a handle and an outer sheath coupled to the handle, the insert system comprising;
a rod configured to fit within the outer sheath and engage at its proximal end the handle; and
a plurality of tools each being demountably attachable to a distal end of the rod.

In one embodiment the plurality of tools comprises at least two tools of different configuration.

In one embodiment the plurality of tools comprise one or more of the tools as described hereinabove in relation to the first aspect.

In a third aspect there is provided a laparoscopic instrument comprising:
a handle;
an outer sheath coupled to the handle; and,
an insert in accordance with the first aspect, the insert being disposed within the outer sheath and operatively coupled at a proximal end with the handle.

In a fourth aspect there is provided a laparoscopic instrument system comprising:
a handle;
an outer sheath coupled to the handle; and,
an insert system according to the second aspect.

In a fifth aspect there is provided a laparoscopic suture system for facilitating laparoscopic surgery, the laparoscopic suture system comprising:
an elongated rod provided at one end with a tool having with a hole through which a suture can pass; and,
a handle coupled to an opposite end of the elongated rod, the rod dimensioned to enable the tool to be located internal of a body undergoing laparoscopic surgery while the handle is located externally of the body.

In one embodiment the tool is movably coupled to the elongated rod and the handle is coupled to the tool to selectively move the tool relative to the rod upon manipulation of the handle.

In one embodiment the tool is pivotally coupled to the rod wherein manipulation of the handle affects a pivotal motion of the tool or a portion thereof relative to the rod.

In one embodiment the laparoscopic suture system comprises a releasable locking mechanism arranged to enable the position of the tool relative to the rod to be releasably locked.

In one embodiment the tool is demountably coupled to the elongated rod wherein rod can be decoupled from the elongated rod when in vivo to enable withdrawal of the elongated shaft from the body while the tip portion remains in vivo and subsequently enabling re-coupling of the tip portion to the elongated shaft upon re-entry into the body.

A sixth aspect provides a tool for a laparoscopic instrument.

BRIEF DESCRIPTION OF THE DRAWINGS

Embodiments of the present invention will now be described by way of example only with reference the accompanying drawings in which:

FIG. 4a is an isometric view of an insert with an alternative linkage mechanism;

FIG. 4b is a view of detail O in FIG. 4a;

FIG. 4c is an end view of the insert shown in FIG. 4a;

FIG. 4d is a view of section R-R of shown in FIG. 4c;

FIG. 5a is a representation of an embodiment of a tool in the form of a needle that can be used with or incorporated in the insert shown in FIG. 2;

FIG. 5b illustrates an embodiment of a tool in the form of a needle which differs from that shown in FIG. 5a by way of its coupling portion;

FIG. 6b depicts an insert incorporating the ski needle shown in FIG. 6a;

FIG. 6c depicts an end portion of the insert shown in FIG. 6b but with the ski needle pivoted with respect to a shaft of the insert;

FIG. 7a is a representation of the tool in the form of a ski needle which is of greater length than that shown in FIG. 6a;

FIG. 7b depicts an insert incorporating the ski needle shown in FIG. 7a;

FIG. 7c depicts an end portion of the insert shown in FIG. 7b but with the ski needle pivoted with respect to a shaft of the insert;

FIG. 8a is a representation of a tool in the form of a ureteric tunneller that may be used with or incorporated in the insert;

FIG. 8b is a representation of a tool in the form of a ureteric tunneller but of a different configuration to that shown in FIG. 8a;

FIG. 8c is a representation of a tool in the form of a ureteric tunneller having a head of different configuration to that shown in FIGS. 8a and 8b;

FIG. 9 is a representation of a tool in the form of a dissector that may be used with or incorporated in the insert;

FIG. 10a is a side view of a tool in the form of a dissector of different configuration to that shown in FIG. 9;

FIG. 10b is an isometric view of the dissector shown in FIG. 10a;

FIG. 10c is an enlarged plan view of a distal end of the dissector shown in FIG. 10a;

FIG. 11a is a side view of a tool in the form of a dissector of different configuration to that shown in FIGS. 9 and 10a;

FIG. 11b is an isometric view of the dissector shown in FIG. 11a;

FIG. 11c is a plan view of a distal end of the dissector shown in FIG. 11a;

FIG. 12 is a representation of a tool in the form of a myoretractor that can be used with or incorporated in an insert;

FIG. 13a is a side view of a tool in the form of a myoretractor of different configuration to that shown in FIG. 12;

FIG. 13b is an isometric view of the myoretractor shown in FIG. 13a;

FIG. 13c is a side view of a tool in the form of a cork screw myoretractor that can be used with or incorporated in an insert in an aligned configuration with a shaft of the insert;

FIG. 13d is an isometric view of the cork screw myoretractor shown in FIG. 13c but with the tool pivoted with respect to the shaft of the insert;

FIG. 14 is a representation of a tool in the form of a cutting edge needle that may be used with or incorporated in the insert;

FIG. 15 is a representation of a tool in the form of a GI retractor that can be used with or incorporated in the insert;

FIG. 16b is a side view of an insert incorporating the ski needle depicted in FIG. 16a;

FIG. 16c is a view of an end portion of the insert shown in FIG. 16b but with the ski needle in a pivoted position with respect to a shaft of the insert;

FIG. 17 is a representation of a tool in the form of a scalpel that may be used with or incorporated in the insert;

FIG. 18 is a representation of a tool in the form of a peeling blade that may be used with or incorporated in the insert;

FIG. 20 is a representation of a coupling portion for a scalpel blade enabling a scalpel blade to be presented at two mutually perpendicular angles;

FIG. 21a is a representation of an insert provided with a tool in the form of a myoma drill and incorporating a further form of linkage mechanism;

FIG. 21b is a view of a portion of the insert shown in FIG. 21a but with the tool pivoted relative to a rod of the insert; and, FIG. 21c is an enlarged plan view of a portion of the linkage mechanism shown in FIG. 21a.

DETAILED DESCRIPTION OF THE PREFERRED EMBODIMENTS

Figure 1:
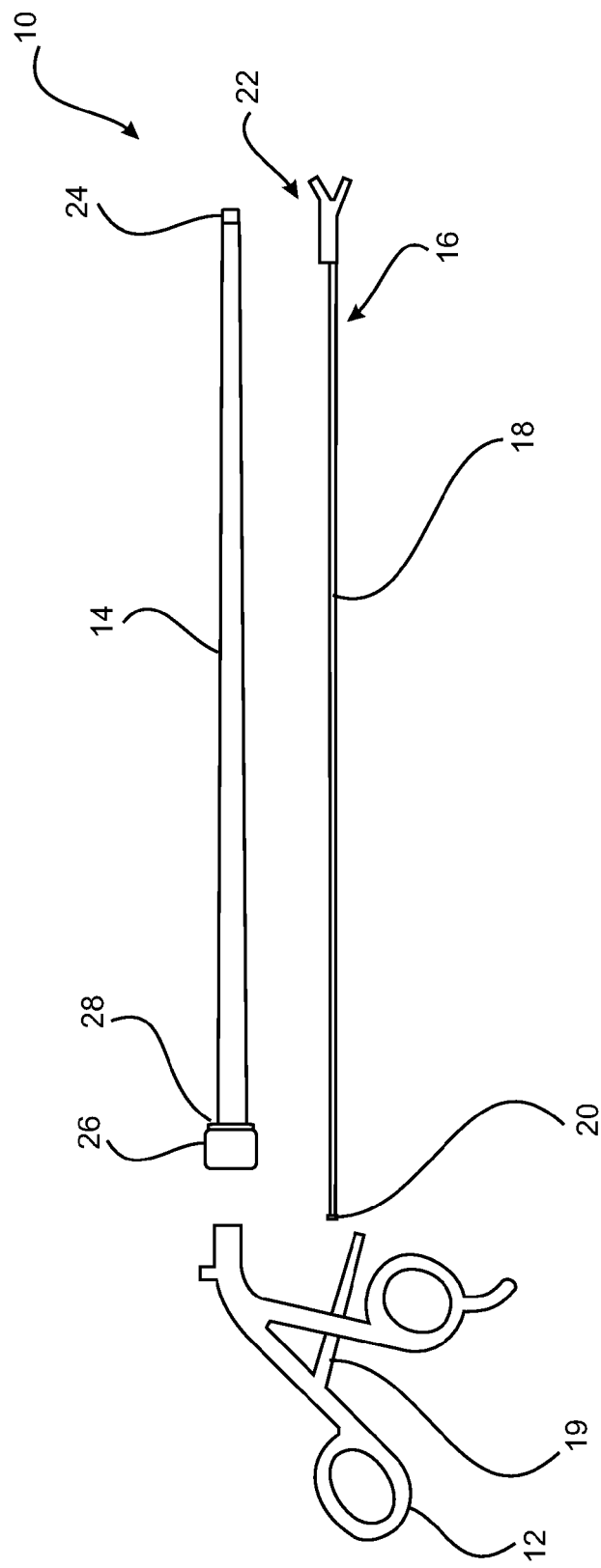
FIG. 1 is a representation of a prior art laparoscopic instrument in a disassembled state.

To provide context to embodiments of the present invention reference is made to FIG. 1 which depicts a conventional manual laparoscopic instrument 10. The instrument 10 comprises three primary components namely a handle 12, an outer sheath 14, and an insert 16. The insert 16 comprises a rod 18 which is provided with a ball 20 at a proximal end and a tool 22 at an opposite distal end. The ball 20 is seated in a socket (not shown) in the handle 12 to provide mechanical coupling between the handle 12 and the insert 16. The handle 12 is formed with two arms or levers 15 that are pivotally coupled together. A finger ring 17 is provided at an end of each arm 15 to enable gripping of the handle 12. A releasable lock mechanism 19 is attached between the arms 15 and is operable to hold the arms 15 at fixed angle relative to each other.

Prior to the insert 16 being coupled to the handle 12, it is inserted into the outer sheath 14 so that the tool 22 is adjacent a distal end 24 of the sheath 14. When in this configuration, the ball 20 of insert 16 extends beyond proximal end 26 of the sheath 14. A screw coupling 28 is provided at the proximal end 26 to enable attachment of the sheath 14 to the handle 12. The insert 16 includes a mechanical linkage system which operates to convert linear motion of the rod 18 within sheath 14 into a pivotal motion of one or more elements of the tool 22.

Thus when the instrument 10 is in an assembled state the insert 16 is disposed within the outer sheath 14 with the tool 22 extending from a distal end 24 and; the ball 20 of insert 16 and coupling 28 of sheath 14 are both coupled to different sections of the handle 12. The handle is manipulated by inserting the thumb and forefinger in respective finger rings 17 and squeezing the rings 17 together or pushing them apart to pivot the arms 15 toward or away from each other. This causes the rod 18 to move linearly within and with respect to the outer sheath 14. This linear motion is translated into a pivoting motion by virtue of the linkage system and activates or otherwise manipulates the tool 22 to perform its intended function. Thus for example in the event that the insert 16 is a forceps, this action will result in jaws of the forceps opening or closing depending on whether the motion of the relative position of the finger rings 17.

The function of the laparoscopic tool 10 is determined by the nature of the insert 16. For any particular surgical procedure a surgeon may have a large range of instruments 10 which differ only in relation to the insert 16 in order to complete the surgical procedure at hand.

Figure 2:
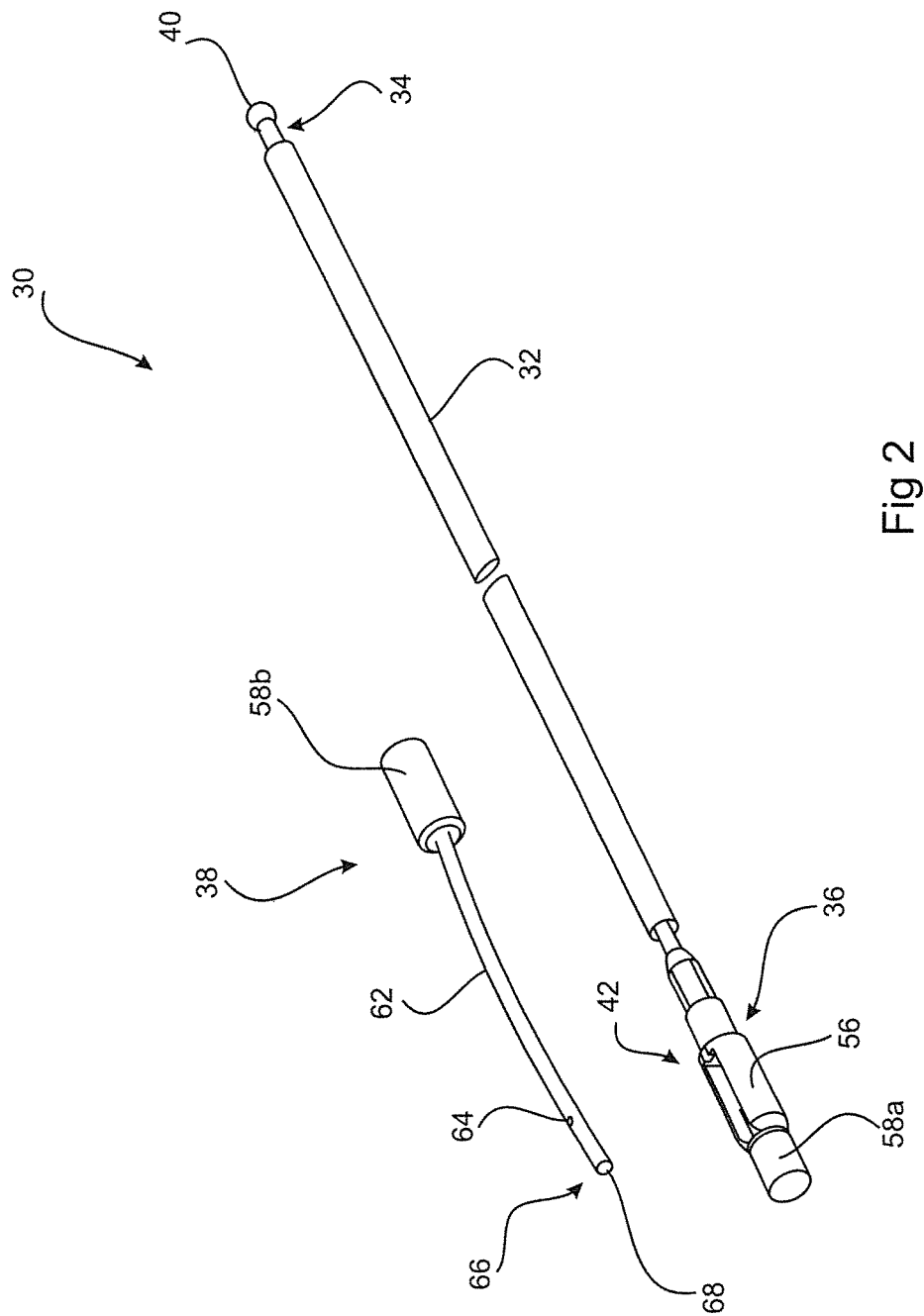
FIG. 2 is a representation of an embodiment of an insert in a disassembled state for a laparoscopic instrument.

FIG. 2 depicts an embodiment of an insert 30 in accordance with the present invention when in a disassembled state. The insert 30 comprises a rod 32 having a proximal end 34 and a distal end 36. The insert 30 also comprises a tool 38 which is demountably coupled to the distal end 36. Proximal end 34 is formed with a ball 40 which is configured to seat and engage in a socket of the handle 12 of a laparoscopic instrument 10. The distal end 36 of the rod 32 is provided with an attachment head 42 to facilitate the attachment of the tool 38.

Figure 3A:
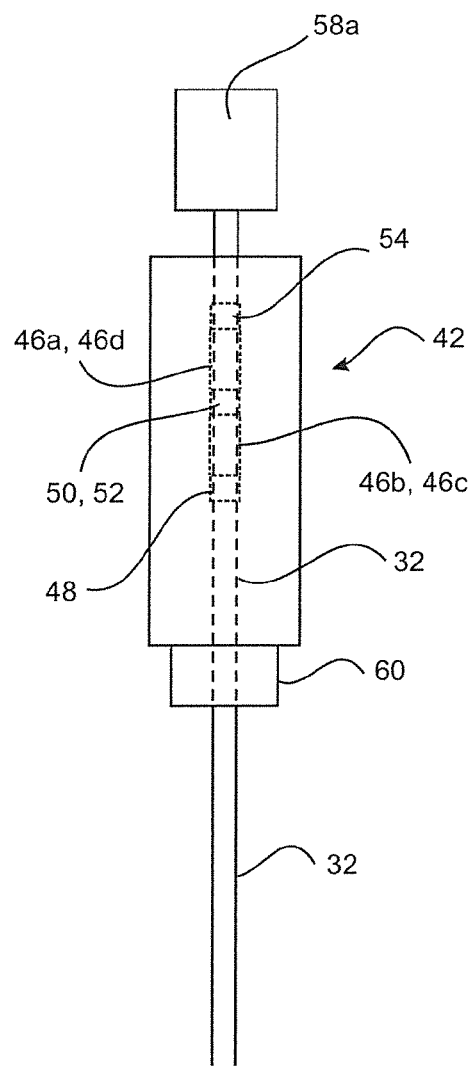
FIG. 3a is a representation of a linkage mechanism incorporated in the insert shown in FIG. 2 when in a first state.
Figure 3B:
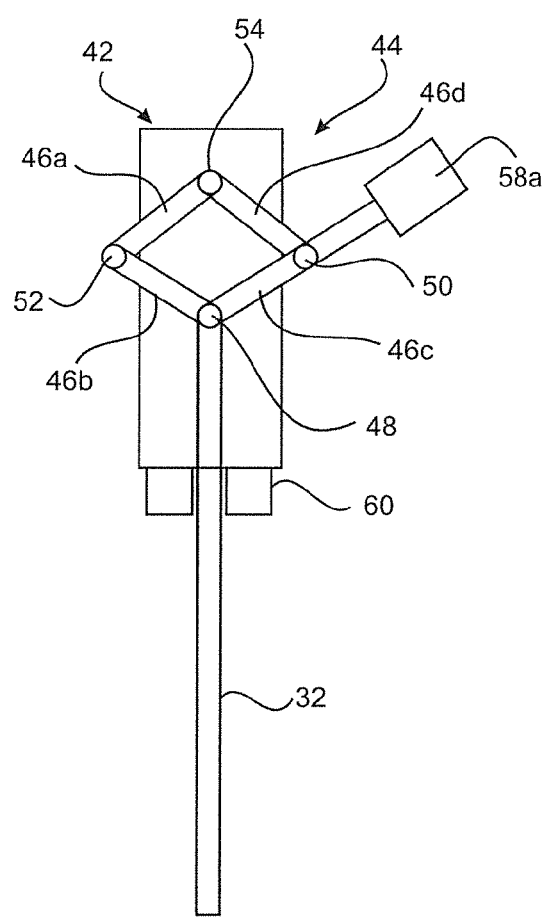
FIG. 3b is a representation of the linkage mechanism incorporated in the insert shown in FIG. 2 when in a second state.

FIGS. 3a and 3b illustrate one form of linkage mechanism 44 for the attachment head 42 that converts the linear motion of the insert 30 (and in particular rod 32) relative to the outer sheath 14 to a pivotal motion. The linkage mechanism 44 comprises four arms 46a-46d that are pivotally coupled together. Specifically arms 46b and 46c are both pivotally coupled to one end of the rod 32 about a pivot point 48. An opposite end of arm 46c is pivotally connected to one end of arm 46d about pivot point 50. Arm 46a is pivotally coupled at one end to the arm 46b via a pivot point 52. An opposite end of the arm 46a and one end of the arm 46d are pivotally coupled to one end of a common pivot pin 54. An opposite end of the pivot pin 54 is held in one arm of a bifurcation of the attachment head 42. The coupling piece 58a is attached to pivot point 50 and extend from a slot created by the bifurcated arm 56. The coupling piece 58a couples with a complimentary coupling piece 58b on the tool 38. A reduced diameter boss 60 extends from an end of the bifurcated arm 56 distant the fixed pivot point 54.

When the insert 30 is attached to the handle 12 and located within the outer sheath 14, the boss 60 fits inside the end of the outer tube 14 while the bifurcated arm 56 extends from the end of the sheath 14. When the handle 12 is manipulated, causing the insert and in particular the rod 32 to move linearly, the linkage mechanism 44 operates to effect a pivotal motion of the coupling piece 58a.

Reverting back to FIG. 2, the tool 38 in this instance comprises a curved suture needle having a curved shaft 62 which extends from the coupling portion 58b. A suture hole 64 is formed near a distal end 66 of the needle. In this instance, the distal end 66 is terminated in a rounded tip 68.

The coupling parts 58a and 58b may be in the form of complimentary screw threads. Alternately the coupling portions 58a and 58b may take many other forms including but not limited to luer lock couplers. Irrespective of the specific nature of the coupling portions 58a and 58b the provision of the coupling portions enables the tool 38 to be interchanged at will.

FIGS. 4a-4d show an insert 30a provided with an alternate linkage mechanism 44a. The insert 30a comprises a tube 33 having a slot 35 at one end creating spaced arms 37a and 37b and an increased outer diameter seat 39. An internal rod 32a extends through a central bore in the tube 33. One end of the tube 33 is provided with a ball 40 that lies in the seat 39. An opposite end of the rod 32a that extends into the slot 35 is bent and pivotally connected to a coupling part 58a by a pivot pin 57. The coupling part 58' is itself connected by a pivot pin 48a to the arms 37a and 37b. The pivot pins 48a and 57 are offset form each other to create a lever mechanism. Thus when the rod 32a is moved linearly relative to the tube 33 the coupling part 58a will pivot about the pivot pin 48a. The rod 32a can be moved linearly relative to the tube 33 by fitting the tube 33 into the sheath 14 and engaging the ball 40 in a socket of the handle 12 of a laparoscopic instrument 10, and subsequently manipulating the handle 12.

FIGS. 5a-5h depict embodiments of other tools that may be demountably coupled to the rod 32 to form different types of inserts 30. FIGS. 5a and 5b depict tools 38a and 38b in the form of suture needles. Both needles 38a and 38b differ from the needle 38 shown in FIG. 2 by the provision of a straight needle shaft 62a and 62b respectively. Otherwise the tool 38a is the same as tool 38. However with the tool 38b, the coupling portion is in the form of a luer lock coupling portion 58'b.

The provision of tools 38 in the form of suture needles is particularly useful for laparoscopic suturing and as explained below has many benefits over prior art laparoscopic suturing.

Prior art laparoscopic suturing requires a laparoscopic needle holder, a laparoscopic grasping forceps, and a suture needle held by the laparoscopic needle holder. A distal end of the laparoscopic needle holders and the suture needle are passed into the body through a trocar. In order to introduce a trocar into the body an incision is first made in the body. The length of the incision is dependent upon the diameter of the trocar. Most trocars used in laparoscopic surgery have an inner diameter of 5 mm or 10 mm. This limits the degree of curvature of a suture needle that can be passed into the body through such trocars. Indeed often the best suture needle for a particular procedure will have a curvature that prevents it from being passed through such trocars.

On possible solution to this problem is to use straight or ski shaped needles. However such needles may not suitable for many suturing situations. A further option to enable the use of a curved needle is to use a larger diameter trocar. But this has the disadvantage of requiring a larger incision. Another solution is to push the needle directly through tissue into the body cavity in which the surgery is being conducted. This runs the risk of the needle breaking and/or become embedded in muscle.

Once the suture needle is located in the body cavity, it is grasped by a laparoscopic needle holder which itself enters the body through a trocar. An intracorporeal laparoscopic needle holder is provided with two jaws to enable the gripping of a suture needle at right angles to the axis of the jaws so that a point of the needle can be driven into tissue or pedicle being sutured. Laparoscopic suturing requires a special skill when performed in this manner. Manipulating the needle into a suturing position when at right angles to the jaws requires precise and steady hand-eye coordination. Any deficiencies in coordination and dexterity may lead to unintentional puncturing or injury of organs or vessels. A straight or a ski needle requires even greater dexterity. The suturing procedure is performed by viewing a TV monitor. After passage through the tissue or pedicle, opposite ends of the suture are put together and a knot is made, either by intracorporeal tying where the knot is made internally by using two graspers; or by extracorporeal tying, where two ends of the suture are taken out through a trocar and a knot is made externally and then passed back through the trocar into the body. By repeating this process a line or bundle of tissue can be sutured and secured.

Inserts in accordance with embodiments of the present invention which incorporate the suture needles 38, 38a and 38b may greatly assist in overcoming the difficulties associated with conventional laparoscopic suturing. This is because the laparoscopic instrument 10 with an insert 30 in accordance with embodiments of the present invention, for example inserts 30 with one of the tools 38, 38a, 38b can be introduced through a standard trocar into the body cavity. The curvature of a standard needle used in prior art laparoscopic suturing can be replicated by inserts 30 by manipulation of the handle 10 which will result in a pivoting of the needle about pivot pin 54. The insert 30 can be arranged so that the suture needle pivots to an angle of 130° to encircle pedicle. Indeed, complete angulation to 180° can be provided by appropriate configuration of the linkage mechanism 44. The overall effect is the same as having a needle of a curve between 130° and 180° but with ability to introduce the needle through a 5 mm or 10 mm trocar. Further, as the suture needle is detachably coupled to the shaft 32 of the insert 30, it is possible to detach and reconnect the needle in vivo to the same or different laparoscopic tools.

Further embodiments of the tools 38 will be described with reference to FIG. 6a-18. In these descriptions the same reference numbers will be used to denote the features that are identical. However where features are generally analogous though not identical the same reference number is used but with the addition of an alphabetic letter suffix and/or a prime (') symbol.

Figure 6A:
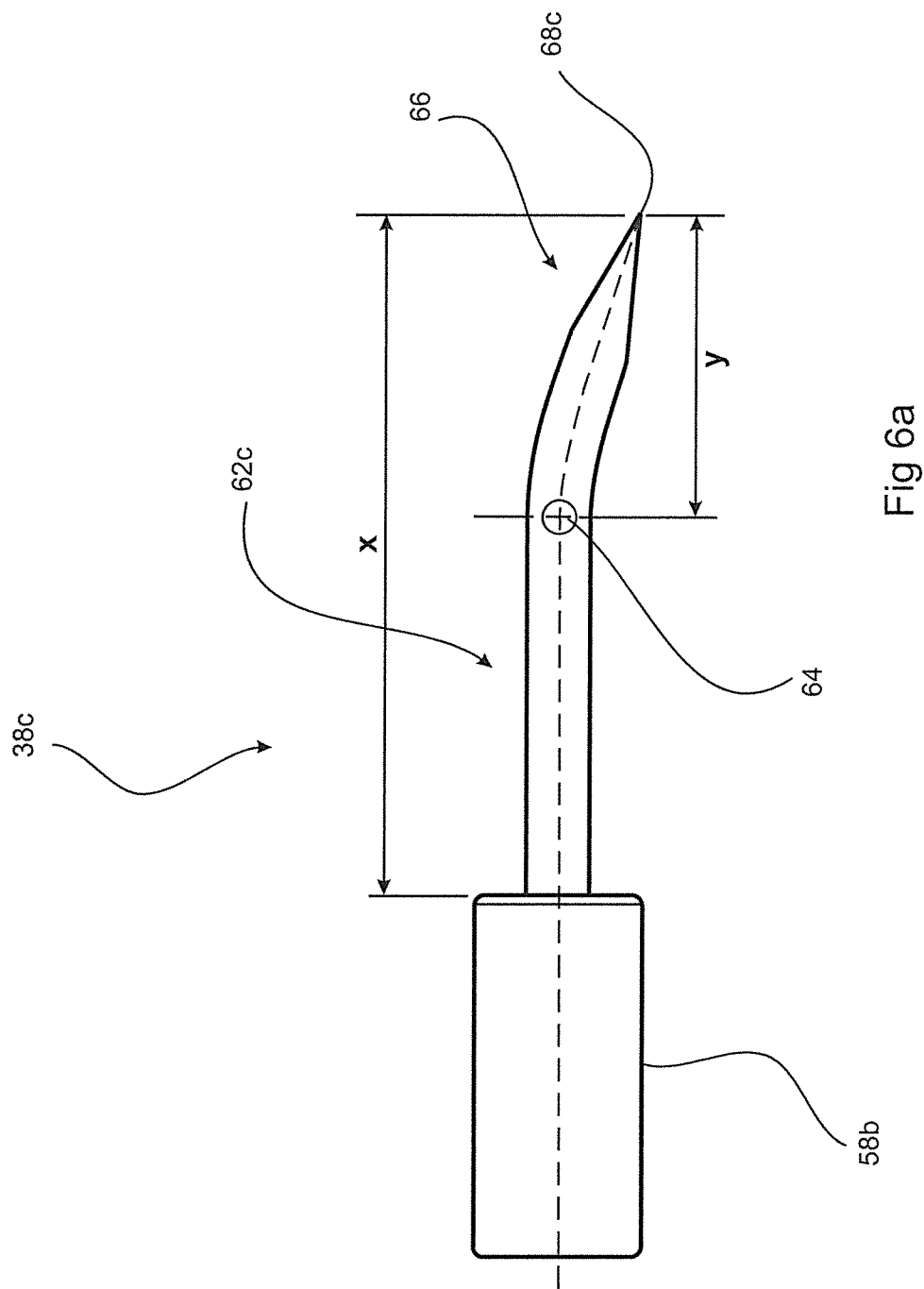
FIG. 6a depicts an embodiment of a tool in the form of a ski needle that can be used with or incorporated in an insert shown in FIG. 2.

FIG. 6a illustrates a further tool in the form of a ski needle 38c, while FIGS. 6a and 6c depict an insert 30c which comprises the ski needle 38c. The ski needle 38c has a curved shaft 62 that extends from a coupling portion 58b and is curved at its distal end 66 terminating in a point 68c. A suture hole 64 is formed just over halfway between the coupling part 58b and the point 68c. In this particular embodiment the shaft 62c extends for a distance x=20 mm from the coupling 58b and the suture hole 64 is a linear distance of y=9 mm form the point 68c. FIGS. 6b and 6c show the insert 32c with ski needle 38c attached to the shaft 32. In FIG. 6b the insert 30c is in an insertion state where the insert 30c coupled to an instrument 10 can be inserted through a trocar into a body cavity. In this state the straight portion of the shaft 62c of the ski needle 38c is parallel and substantially co-linear with shaft 32. FIG. 6c shows a distal end of insert 30c in an active state where the needle 32c has been pivoted by about 120° and being used to suture tissue.

Figure 7A:
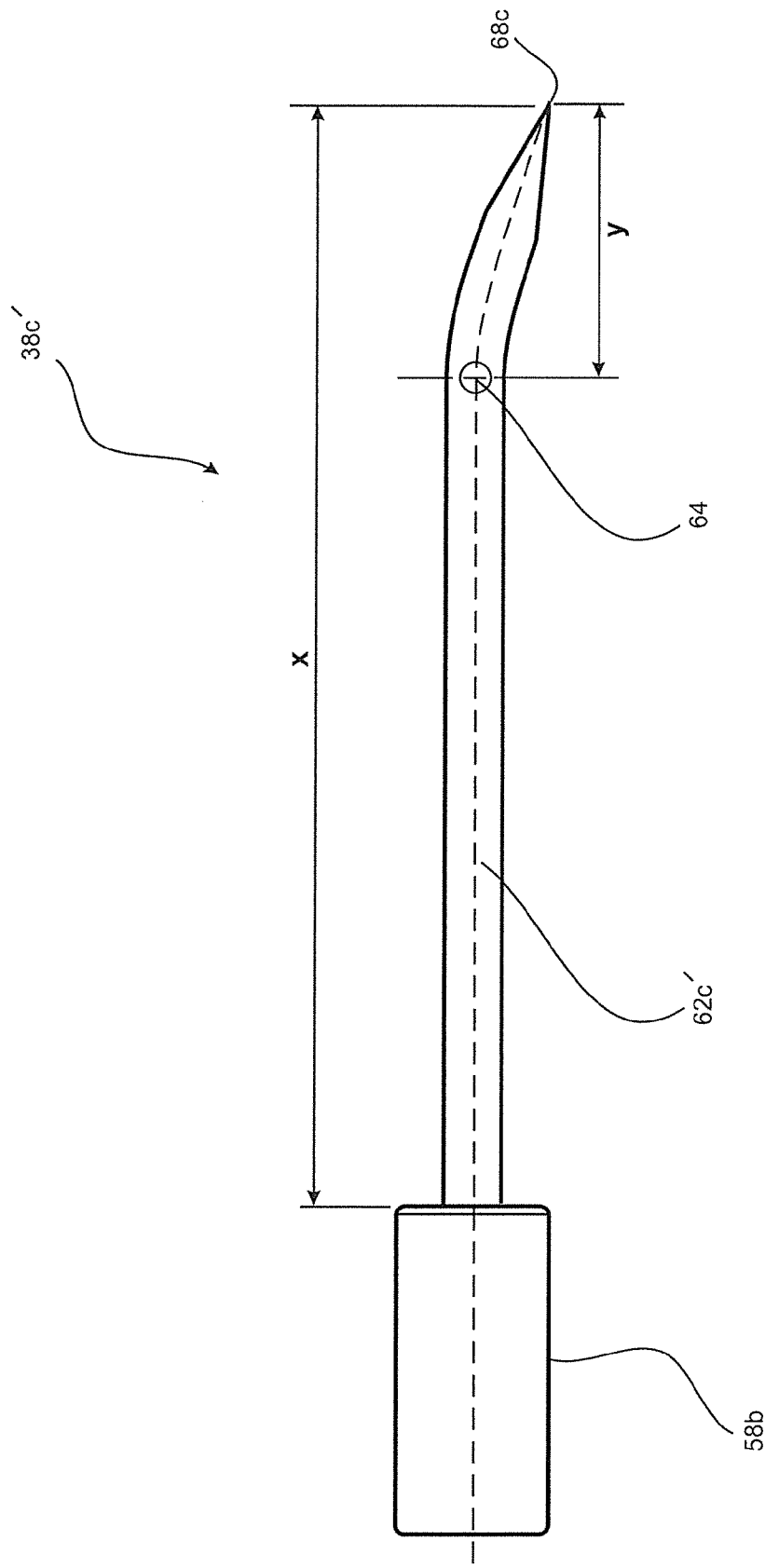

FIGS. 7a-7c illustrates a ski needle 38c' and associated insert 30c' that differs from the ski needle 38c and insert 32c of FIGS. 6a-6c only in its increased overall length. In the ski needle 38c' the distance x=35 mm.

FIGS. 8a-8c illustrate further tools in the form of ureteric tunnellers 38d, 38d' and 38d" (hereinafter referred to in general as "tunnellers"). Each of the tunnellers 38d and 38d' comprises a coupling portion 58b at one end, an intermediate shaft 62d/62d' provided with a suture hole 64, and a spherical end or tip 68d. The spherical end or tip 68d has a diameter several times larger than that of the corresponding shaft 62d or 62d'. The tunnellers 38d and 38d' differ only in the configuration of their respective shafts. In the tunneller 38d, a straight shaft 62d extends between the coupling portion 58b and the tip 68'. However in the tunneller 38d', a curved shaft 62d' extends between coupling portion 58b and tip 68'.

The tunneller 38d" differs from tunneller 38d by way of the shape of its tip 68d". In the tunneller 38d" the tip 68d" is of an ellipsoid shape rather than being spherical. The shaft 62d" of the tunneller 68d" can be made to various different lengths, such as for example about 30 mm or 50 mm. In one embodiment of the tunnellers the suture hole 64 may be about 17 mm form a distal end of the tip 68. In one variation the shaft of the tunneller 68d" can be curved rather than straight.

Ureteric injuries can occur during laparoscopic hysterectomy and in surgery involving pelvic side walls. One precaution taken to prevent ureteric injuries involves dissecting out and displaying the uterus, a procedure that in itself may cause ureteric damage. Another is to insert ureteric cannulas to provide a tactile indicator of the position of the ureter. Yet another method is to insert an illuminated ureteric cannula into the ureter.

The tunnellers described may be used to reduce the risk of ureteric injuries. One use of the tunnellers is as follows. Firstly, the tunneller is connected to the rod 32 to form an insert 30. The insert 30 is then coupled to a standard laparoscopic instrument 10. The lateral pelvic wall peritoneum is pulled up and a small incision is made in it over the underlying ureter. The tunneller is angled to run parallel to the ureter and the spherical/ellipsoid tip 68 is inserted into the incision and pushed forward and moved in a semi-circular motion to free the peritoneum over the underlying ureter. When a predetermined length of ureter is freed under the peritoneum, the peritoneum underlying the spherical/ellipsoid tip 68 is incised and suture material previously threaded through suture hole 64 is pulled out. The tunneller is then withdrawn leaving the suture material to act as a visual marker to the position of the ureter. A colored and dissolvable suture material such as 10 vicryl may be used.

The tunnellers can be made of a non-conducting plastic material to allow electrosurgical energy to be used to incise the peritoneum over the tunneller.

The ureteric tunneller can be used to free deeper structures in the lateral pelvic side walls such as the internal iliac arteries and veins, to obtain lymph nodes from the pelvic side walls for biopsy. A suture can be placed around an organ or vessel in this position.

The ureteric tunneller can also be used in a similar manner to free tissue around other organs in the abdominal and pelvic cavities. The suture hole provides the placement of a suture around a tissue or vascular pedicle and acts as a marker for the surgeon.

FIGS. 9-11c illustrate various embodiments of tools in the form of dissectors. FIG. 9 shows a basic form of the dissector 38e. The dissector 38e comprises a coupling portion 58d at one end to enable coupling to the coupling portion 58a of a rod 32. A shaft 62e extends from the coupling portion 58b and terminates in a reduced thickness tip 68e which provides a planar dissecting surface 67. The shaft 62e is wider than corresponding shafts of the previously described tools to provide a broader base for the dissecting surface 67. In this regard, the dissecting surface 67 may be made for example of a width of between 5 mm to 10 mm. The dissecting surface is a planar surface which is sloped relative to a longitudinal axis of the tool 38e. The reduced thickness tip 68e and the surface 67 terminate is a straight edge 69 that lies perpendicular to the longitudinal axis of tool 38e. A suture hole 64 is provided behind the tip 68e to receive a suture or tape. It is envisaged however in an alternate embodiment that the dissector 38e can be provided without a suture hole 64.

Laparoscopic surgery involves the displaying and identification of tissue. Trauma and injuries to various tissue and organs result from inadequate dissection. In conventional laparoscopic surgery, the dissection is performed by scissors and forceps. These provide narrow and sharp presenting points which can result in accidental injury to tissue and blood vessels notwithstanding expertise of the surgeon. Embodiments of the inserts 30 that comprise the dissector 38e can assist in reducing injury due to the substantial (i.e. broad) dissecting tip 68e. This provides a large presenting part to reduce the risk of penetration of tissue or blood vessel. The provision of the suture hole 64 behind the dissecting tip 68e enables a suture or tape to be placed around or behind the tissue or organ being dissected.

FIGS. 10a-10c show a modified form of dissector 38e. The dissector 38e' differs from the dissector 38e by the: omission of the suture hole 64; curvature of the reduced thickness tip 68e; and, shape of the shaft 62e. The tip 68e' is tapered in thickness in a direction away from the coupling 58b and formed with a plurality of contiguous planar surfaces 67 on a concave side of the tip 68e. The shaft 62e' is also formed with a dovetail shaped cut out 71. The dissector is used with the curved tip 68e' facing down so that tissue can be pushed away with the tip 68e'. The slot 71 can be placed on a corner of a uterus and used as a traction hook.

FIGS. 11a-11c show a dissector 38e" that differs from dissector 38e' only by the provision of a linear slot 73 in the tip 68e". The slot is open at one end and terminates in a region near the inner most of planar surfaces 67. In one embodiment the slot 73 may have a length in the order of 10 mm and a width of about 0.6 mm. The slot 73 is used to allow placement of a piece of mesh which can be pulled out and placed over tissue or organs.

FIG. 12 depicts a tool 38f in the form of a myoretractor. The myoretractor 38f comprises a coupling portion 58b at one end, a tapered shaft 62f extending from the coupling portion 58b, and terminating in a conically tapered point 68f. A suture hole 64 is formed behind the point 68f. Current laparoscopic material removal of fibroids requires the use of a corkscrew type instrument that is used to manipulate exposed fibroids. After an incision on a uterine wall above a fibroid is made, the fibroid is exposed and the corkscrew instrument is screwed into the fibroid. Traction is then placed on the fibroid and with counter traction the fibroid is pulled out of the uterine wall. Unfortunately, often a conventional 5 mm pitch corkscrew does not provide enough embedment or grip in the fibroid tissue, and traction results in the corkscrew instrument being pulled out of the fibroid tissue. Larger pitch corkscrews of say 10 mm diameter can be used but would require a larger skin incision. Repeated expulsion and reinsertion of the corkscrew may result in fibroid fragmentation. This is manifested by bleeding and the scattering of pieces of fibroid in the abdominal and pelvic cavities.

During laparoscopic hysterectomy, the uterus is pulled from one side to the other to expose uterine vessels for ligation and division. Typically a 5 mm grasping forceps is used to achieve this. Unfortunately, the size of the forceps jaw does not allow for strong traction to be applied to the uterine muscle. This results in the forceps being pulled off the uterine muscle requiring reapplication. Again a larger 10 mm forceps can be used but this requires a larger skin incision.

An insert 30 which comprises the myoretractor 38f enables the shaft 62f to be angulated (i.e. pivoted with respect to the rod 32). Thus the laparoscopic instrument 10 having an insert 30 provided with the myoretractor 38f is placed into a trocar port and then the myoretractor 38f can be angulated by manipulation of the handle 12 across the fibroid or uterus to allow the point 68f to be driven into the fibroid or uterus. This enables the insert 30 to hook in and onto the fibroid or uterus. Traction of variable degrees can be applied without the possibility of the myoretractor 38f being pulled off like the corkscrew instrument. The shaft 62f of the myoretractor 38f is made with an outer diameter sufficient to provide adequate traction by virtue of being driven a sufficient distance into the fibroid of a uterus.

FIGS. 13a and 13b depict a further form of myoretractor 38f'. The myoretractor 38f has a tip 68f in the configuration of a broad hook. The shaft 62f of myoretractor 38f is formed from cylindrical stock of constant diameter and machined to form an inboard elongated recess that terminates in the hook tip 68f. The myoretractor 38f is used in the same way as the myoretractor 38f but the hook tip 68f provides an alternate traction mode. The hook tip 38f may take the form of a rice hook or sickle hook.

FIGS. 13c and 13d illustrate how the functionality of a convention cork screw instrument is enhanced by utilization with or incorporation into an insert 30f". The insert 30f" is provided with a detachable corkscrew tool 38g". Due to the ability of the insert 30f" to provide angulation of the tool 38f" a double grip is now available. A first grip is achieved in a conventional manner by using the insert 30f" with the tool 38f" in line with the shaft of the insert 30f", as shown in FIG. 13c. A second grip is achieved by subsequently manipulating an instrument 10 to which the insert 30f" is attached to pivot the tool 38f" relative to the shaft as shown in FIG. 13d.

FIG. 14 depicts a tool 38g in the form of a cutting edge needle. The cutting edge needle 38g comprises a coupling portion 58b, a shaft 62g extending from the coupling portion 58b and terminating in a cutting edge 68g. The cutting edge 68g comprises planar cutting surfaces 70 that taper to a central tip or point 72f. Optionally, a suture hole (not shown) can be formed through the shaft 62g behind the cutting edge 68g. The cutting edge needle 58g may be used in a similar manner as the needles 38, 38a and 38b but in situations where the needle is required to cut through tissue.

FIG. 15 depicts a tool 38h in the form of a gastro-intestinal ("GI") retractor.

During laparoscopic GI surgery, the liver, stomach, small and large intestines may require traction or reflection to expose the surgical field. Typically this is performed by the use of graspers or blunt probes.

The tool 38f consists of a blunt or rounded presenting end 68h provided at an end of a shaft 62h. The shaft may be in the form of a planar shaft or plate; or, a shaft of circular cross section. Also the shaft may be made to different lengths. One or more (and in this particular illustrated embodiment three)

scallops 74 are formed on the inner surface of the shaft 62h, allowing for the retracted tissue to be retracted without excessive pressure being applied to it. Behind the presenting part, a 2 mm-8 mm or larger suture hole 64 is provided. This hole allows for a suture material or tape to be passed as the GI retractor traverses the area or organ of dissection. Typically, a suture or tape can be passed across the stomach, renal vessels or any other organ or tissue mass.

In a broad sense each of the tools 38-38h when provided with a suture hole can be considered to be a suture tool or device.

As embodiments of the instrument 10 can provide angulation approaching 180°, and easily up to at least 150°, a long retraction bar can be introduced into the abdomen and then angulated to sweep up the bowel and hold it from falling into the line of operation. In the same way, material can be wrapped around a bar, similar to a rolled up flag, and then unfolded to place over tissue. A large collection bag can likewise be introduced and placed into the abdominal cavity. A large deflated balloon can be introduced and angulated into position and then blown up to protect organs and tissue during operations. It is also possible to leave such inflated balloons in the pelvis or around organs for a few days to prevent adhesion forming.

Figure 16A:
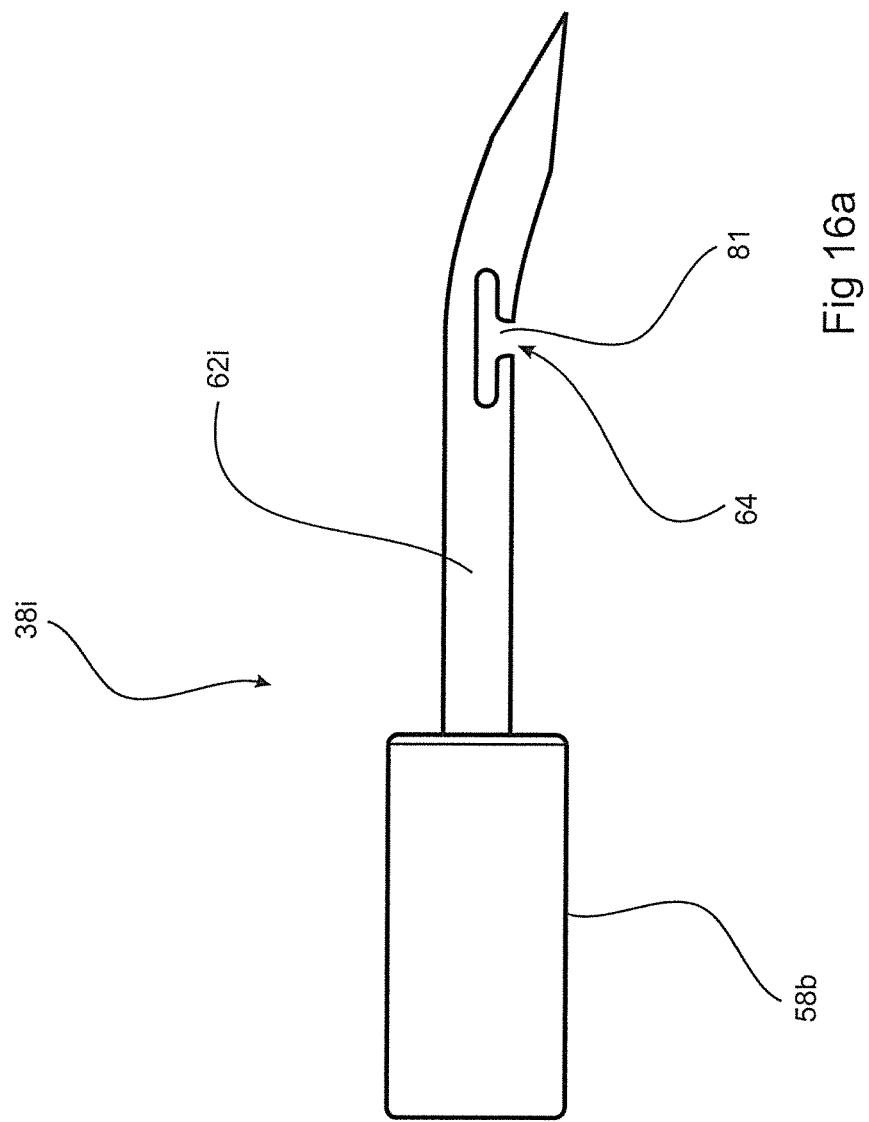
FIG. 16a is a side view of a tool in the form of a ski needle provided with a suture slot that may be used with or incorporated in an insert.

FIGS. 16a-16c illustrate a ski needle 38i and associated insert 30i. The ski needle 38i differs from that depicted in FIGS. 6a-6c by replacement of the suture hole 64 with a slot 64i. The slot 64i extends longitudinally of the shaft 62i and is closed at its opposite longitudinal ends. Slot 64i may be in the order of 4 mm in length and approximately 0.6 mm in width. The slot has a transverse opening 81 extending from a midpoint of the length of the slot 64i. In one embodiment the slot 81 has a width of approximately 1 mm.

The provision of the slot 64i allows for suture material to be selectively engaged and disengaged from the needle 38i during tissue suturing. Further, the suture material is able to slide in the slot 64i in either a forward or a backward direction. The slot 64i allows for continuous suturing as the suture is introduced or extracted from the slot 64i as the needle is introduced or withdrawn through tissue. When sewing in a forward direction the suture is introduced into the slot 64i before the needle is passed through tissue. The suture would then be extracted from the slot 64i via the opening 81 after passing through the tissue but before the needle is withdrawn. In a reverse procedure where a needle 38i is introduced first and the suture engaged into the slot, the suture would be pulled through the tissue and then disengaged from the slot 64i before the next pass. This now enables a surgeon to perform a mattress stitch in a manner substantially easier and quicker than using a conventional needle and needle holder.

In all of the embodiments of tools described hereinbefore which have or may have a suture hole 64, the hole may be replaced with a slot 64i as described hereinabove to enable continuous suturing. The term "suture apertures" is used as a general term to cover and refer to both a suture hole 64 and a suture slot 64i.

Tools provided with a suture slot 64i can be used with all suture materials. Moreover, such tools may be used with a modified barbed suture in which the suture is formed with one or more loops at a free end that can selectively engage the suture slot 64i through the opening 81. The provision of two or more adjoined loops at one end of the suture provides a degree of redundancy in the event that one of the loops engaged with the suture slot 64i breaks.

Insulation can be applied to any of the tools 38 to allow cautery to be performed (specifically a needle tool such as needles 38a or 38b to perform ovarian drilling) or electrical cautery dissection to be performed on the tool 38, thereby protecting the tissue behind the tool 38, for example the ureteric tunneller, where peritoneum is incised over it.

FIG. 17 depicts an insert 30j provided with a detachable tool 38j in the form of a scalpel. The tool comprises a scalpel holder 90 having a coupling 58b at one end and shaft 62j that extends from the coupling 58b and is configured to releasable hold a scalpel blade 92. The ability to pivot the scalpel blade 92 in vivo by manipulating the instrument 10 (i.e. opening and closing the handle 12) to which the insert 30j is attached assists in morcellation of large uterus and fibroids.

FIG. 18 depicts an insert 30k provided with a detachable tool 38k in the form of a peeling blade 94. The peeling blade 94 has a configuration similar to a potato peeler. The blade 94 has two mutually facing longitudinal cutting edges 96a and 96b on opposite sides of a longitudinal slot 98. The thickness of tissue that can be cut/sliced by use of the peeler blade 94 is dependent on the configuration of the blade 94 including the width of a slot 98. The insert 30k is used in a similar manner and for the same purpose as the insert 30j.

Figure 19:
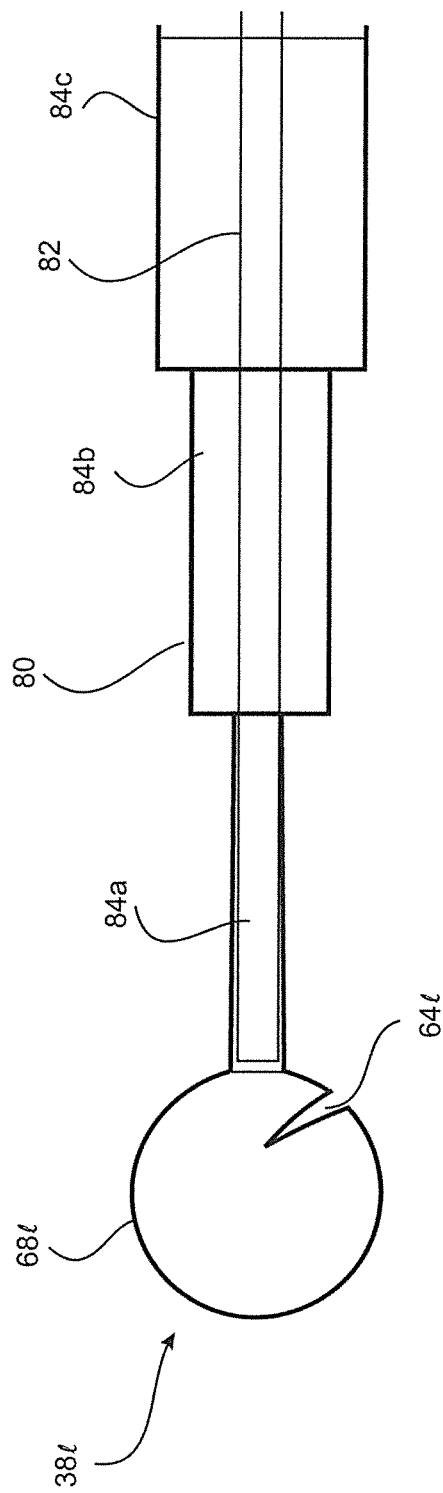
FIG. 19 is a representation of a tool in the form of a telescope and dilator that may be used or incorporated in the insert.

FIG. 19 depicts a tool 38l in the form of a mesh tunneller that may be incorporated or otherwise attached to an associated insert 30 for incorporation with a laparoscopic instrument. The tool 38l is provided at a distal end with spherical tip 68l that is attached to a telescopic shaft 80. The shaft 80 is telescoped in and out by an internal steel cable or wire 82 that can be wound in or out from a modified handle of the laparoscopic instrument 10. Winding the cable 82 out causes relative extension of tubes 84a, 84b and 84c which together form the telescopic shaft 80. Winding the cable 82 in results in the tubes 84a, 84b and 84c retracting successively into each other. The spherical tip 68l can be provided with a suture opening 64l. The opening 64l may be in the form of a slot that opens onto an external surface of the spherical tip 64l; or a through hole.

The tool 38l is incorporated as a part of a ureteric tunneller similar to those depicted in FIGS. 8a-8c and is used as follows. The ureteric tunneller can be used to tunnel a channel beside the rectum for the sacrum promontory to the vagina or cervix for treatment of genital prolapsed involving the uterus and vagina. Mesh is attached to the vaginal vault or cervix and placed in a channel created beside the rectum in the retroperitoneal space and then attached by sutures or staples to the anterior spinal ligament over the sacral promontory. This procedure can be achieved by open surgery or by laparoscopic surgery.

Typically in the prior art the channel is created by dissecting open a tract beside the rectum and closed by suturing after a mesh is secured to the vagina and sacrum. This is time consuming and requires advanced laparoscopic suturing skills if performed by the laparoscopic route.

The tool 38l enables creation of a channel to place mesh without open dissection and closure by suturing of the channel created. This can be used to tunnel under the peritoneum from the sacral promontory to the vagina or cervix. The spherical tip 68l forms an advancing dissector head and can be attached to either a fixed length shaft or a telescopic shaft 80 as shown in FIG. 19. The shaft can be made from metal or plastic and is capable of being bent but is able to straighten to pass through a 10 mm trocar during laparoscopy. This may be formed as either reusable or single use. After the mesh tunneller has traversed the channel, an incision is made over the tip 68l to allow it to be exposed. A suture loop tied to a mesh is looped about the slot 64l and secured to the narrower shaft 80. The suture is pulled through the channel together with the mesh and then the mesh is stitched to the sacral.

FIG. 20 depicts a form of coupling piece 58b' that may be used to support scalpel blades at different angles. The coupling 58b' is a modified form of the coupling 58b shown in FIG. 17 which supports the scalpel blade 92. With the coupling 58b', a shaft 62j' is formed with a substantially rectangular cross sectional shape with blade holders 100a and 100b on two mutually perpendicular sides of the shaft 62j'. The blade holders 100a and 100b are each able to support a scalpel blade (not shown). Of course however only one scalpel blade will be coupled to the coupling 58b' at any one time.

FIGS. 21a-21c depicts an insert 30m with a detachable tool 38m in the form of a myoma drill. The tool 38m is provided with a coupling 58b at its proximal end arranged to engage the coupling 58a. The coupling 58a is pivotally attached to the rod 32 via a linkage mechanism 44m.

The coupling between the coupling parts 58a and 58b may be in the form of a screw thread, lure lock, or other type of coupling. The linkage mechanism 44m comprises a cam plate 104 (see in particular FIG. 21c) having a large circular portion 106 and an integral small circular portion 108. The two portions 106 and 108 have centres that are axially aligned but are formed with holes 110 and 112 respectively which are axially offset from each other. The large circular portion 106 is also formed with an inboard arcuate slot 114. A pivot pin 54m passes through the hole 110 and into attachment head 42m of the insert 30m. Rod 32 is attached to the small diameter portion 108 of the cam plate 104 by a further pivot pin 116 that extends through the hole 112. A cam guide 118 extends transversely from the coupling part 58a and through the slot 114. Insert 30m is received inside a sheath 14 with the ball 40 arrange to engage the handle 12 and the head 42m arranged to abut the distal end 24 of the sheath 14. On actuation of the handle 12, the rod 32 slides relative to the sheath 14 and due to the offset nature of the holes 110 and 112 and the engagement of the guide 118 in the slot 114 the tool 38m will pivot about the pivot pin 54m.

With the advent of single port laparoscopic surgery various combinations of the tools 38 and associated inserts 30 can be used.

Currently, single ports laparoscopy consists of a 25 to 35 mm port with three instrument channels. A larger central port is for a camera and two lateral ports for instruments. Laparoscopic instruments are inserted and removed as the operation demands. This can be time consuming and require crossing over of instruments rather than withdrawing and insertion of instruments to save time.

Current single use ports do not rotate and instruments have to be pulled in and out and exchange. In embodiments of the present invention rotating ports can be used enabling the desired instrument 10 and corresponding insert 30 to be brought into the desired position for use.

Also embodiments of the various described suture needles would eliminate needle introduction and needle handling during single port suturing.

Modifications and variations to the tools, systems and instruments disclosed herein that would be apparent to those of ordinary skill in the art are deemed to be within the scope of the present invention the nature of which is to be determined by the above description and the appended claims.

The invention claimed is:

1. A suturing insert for a laparoscopic instrument having a selectively lockable handle and an outer sheath coupled to the handle, the insert comprising:
a rod configured to fit within the outer sheath and engage at its proximal end the handle, wherein locking of the handle limits sliding motion of the rod with respect to the sheath;
a linkage mechanism disposed at a distal end of the rod, the linkage mechanism comprising a rotatable tool portion and a cam plate, the cam plate coupled to the rod at a first pivot point and coupled to the rotatable tool portion at a second pivot point, the cam plate comprising an arcuate slot disposed adjacent the second pivot point, the rotatable tool portion comprising a cam guide disposed within the arcuate slot; and
a suturing needle coupled to the rotatable tool portion of the linkage mechanism,
the first and second pivot points and the cam guide configured to convert sliding motion of the rod relative to the outer sheath to pivoting motion of the rotatable tool portion and suturing needle relative to the outer sheath,
the linkage mechanism further comprising an insertion state wherein longitudinal axes of the rod and needle are aligned to enable the needle and at least a portion of the outer sheath to be passed through a trocar into a body cavity, and wherein, in the insertion state, the second pivot point is offset from the longitudinal axis of the rod, and
wherein, in the insertion state, the cam guide is positioned abutting a first end of the arcuate slot.

2. The suturing insert according to claim 1, wherein the first and second pivot points and the cam guide are configured to convert sliding motion of the rod relative to the outer sheath to pivoting motion of the rotatable tool portion and suturing needle relative to the outer sheath of at least 150°.

3. The suturing insert according to claim 1 wherein the needle is provided with a suture aperture opening for receiving a suture.

4. The suturing insert according claim 3 wherein the suture opening is either a suture hole or a suture slot wherein the suture slot extends along a length of the needle and is provided with an opening enabling a suture material to enter the suture slot.

5. The suturing insert according to claim 1 wherein the needle comprises a shape that is able to pass through a trocar having a 10 millimeter inner diameter.

6. The suturing insert according to claim 1 wherein the needle comprises a straight shaft.

7. The suturing insert according to claim 1 wherein the needle comprises a curved shaft.

8. The suturing insert according to claim 1 wherein a distal end of the needle: (a) tapers conically to a point; (b) tapers linearly to a point to produce a cutting edge; or (c) is provided with a rounded end.

9. The suturing insert according to claim 1 wherein the needle comprises a shape that is able to pass through a trocar having a 5 millimeter inner diameter.

10. The suturing insert according to claim 1 wherein the needle comprises a substantially straight shaft and a curved distal end.

11. The suturing insert according to claim 1 wherein the needle is removably coupled to the rotatable tool portion of the linkage mechanism, and the suturing insert further comprises a dissector removably coupleable to the rotatable tool portion of the linkage mechanism, the dissector comprising a shaft, a reduced thickness tip at a distal end of the shaft and a straight edge at a distal end of the tip lying perpendicular to a length of the shaft.

12. The suturing insert according to claim 11 wherein the shaft of the dissector is provided with a slot extending along a longitudinal axis of the shaft and proximal to the tip, the slot comprising a base and an opening, the base extending further along the longitudinal axis than the opening.

13. The suturing insert according to claim 11 wherein the reduced thickness tip of the dissector has at least one planar surface.

14. The suturing insert according to claim 13 wherein the reduced thickness tip of the dissector is curved in configuration.

15. The suturing insert according to claim 13 further comprising a longitudinal slot formed in the reduced thickness tip of the dissector and opening onto the straight edge of the dissector.

16. The suturing insert according to claim 1 wherein, in a fully pivoted state, the cam guide is positioned abutting a second end of the arcuate slot.

17. An insert system for a laparoscopic instrument having a selectively lockable handle and an outer sheath coupled to the handle, the insert system comprising;
a rod configured to fit within the outer sheath and engage at its proximal end the handle, wherein locking of the handle limits sliding motion of the rod with respect to the sheath;
a linkage mechanism disposed at a distal end of the rod, the linkage mechanism comprising a rotatable tool portion and a cam plate, the cam plate coupled to the rod at a first pivot point and coupled to the rotatable tool portion at a second pivot point, the cam plate comprising an arcuate slot disposed adjacent the second pivot point, the rotatable tool portion comprising a cam guide disposed within the arcuate slot; and
a plurality of tools each being demountably attachable to the rotatable tool portion of the linkage mechanism,
the first and second pivot points and the cam guide configured to convert sliding motion of the rod relative to the outer sheath to pivoting motion of the rotatable tool portion relative to the outer sheath,
the linkage mechanism further comprising an insertion state wherein longitudinal axes of the rod and rotatable tool portion are aligned to enable one of the plurality of tools attached to the rotatable tool portion and at least a portion of the outer sheath to be passed through a trocar into a body cavity, and wherein, in the insertion state, the second pivot point is offset from the longitudinal axis of the rod, and
wherein, in the insertion state, the cam guide is positioned abutting a first end of the arcuate slot.

18. The insert system according to claim 17 wherein the plurality of tools comprises at least two tools of different configuration.

19. The insert system according to claim 17 wherein the plurality of tools comprise two or more of the tools selected from the group consisting of: a suture needle; a ureteric tunneller having a straight shaft provided with a spherical tip; a ureteric tunneller having a straight shaft provided with an ellipsoid tip; a ureteric tunneller having a curved shaft provided with a spherical tip; a ureteric tunneller having a curved shaft provided with an ellipsoid tip; a dissector; dissector having a shaft, a reduced thickness tip at a distal end of the shaft and a straight edge at a distal end of the tip lying perpendicular to a length of the shaft; a myoretractor having either a straight shaft or a corkscrew shaped shaft; a myoretractor having a straight shaft and a hook at a distal end of the shaft; a scalpel; and a peeling blade provided with a longitudinal slot, the slot having mutually facing longitudinal cutting edges; any of the above tools having a suture slot, wherein the suture slot extends along a length of the tool and is provided with an opening enabling a suture material to enter the suture slot.

20. The insert system according to claim 17 wherein each of the plurality of tools comprises a shape that is able to pass through a trocar having a 10 millimeter inner diameter.

21. The insert system according to claim 17 wherein, in a fully pivoted state, the cam guide is positioned abutting a second end of the arcuate slot.

* * * * *